US012749192B2

(12) United States Patent
Bard et al.

(10) Patent No.: US 12,749,192 B2
(45) Date of Patent: Sep. 29, 2026

(54) BOWEL SEGMENTATION SYSTEM AND METHODS

(71) Applicant: Motilent Limited, London (GB)

(72) Inventors: Andrew Bard, London (GB); Benjamin Barrow, Welwyn Garden City (GB); Alexander Menys, London (GB)

(73) Assignee: Motilent Limited, London (GB)

( * ) Notice: Subject to any disclaimer, the term of this patent is extended or adjusted under 35 U.S.C. 154(b) by 252 days.

(21) Appl. No.: 18/599,573

(22) Filed: Mar. 8, 2024

(65) Prior Publication Data

US 2024/0303816 A1 Sep. 12, 2024

Related U.S. Application Data

(60) Provisional application No. 63/489,363, filed on Mar. 9, 2023.

(51) Int. Cl.

*G06T 7/00* (2017.01)
*A61B 5/00* (2006.01)

(Continued)

(52) U.S. Cl.

CPC ............ *G06T 7/0014* (2013.01); *A61B 5/055* (2013.01); *A61B 5/4255* (2013.01); *G06T 7/11* (2017.01); *G06T 7/136* (2017.01); *G16H 30/20* (2018.01); *G16H 50/50* (2018.01); *G06T 2200/24* (2013.01); *G06T 2207/10081* (2013.01);

(Continued)

(58) Field of Classification Search

CPC ......... G06T 7/0014; G06T 7/11; G06T 7/136; G06T 2200/24; G06T 2207/10081; G06T 2207/10088; G06T 2207/10132; G06T 2207/20081; G06T 2207/20092; G06T 2207/30028; G06T 7/0012; A61B 5/055; A61B 5/4255; G16H 30/20; G16H 50/50

See application file for complete search history.

(56) References Cited

U.S. PATENT DOCUMENTS

| | | | | |
|---|---|---|---|---|
| 6,343,936 B1 * | 2/2002 | Kaufman | ............ | G06V 10/147 128/920 |
| 8,189,890 B2 * | 5/2012 | Summers | ............... | G16H 15/00 382/128 |

(Continued)

OTHER PUBLICATIONS

Y. Ziselman, F. H. Shinnawi, M. -L. Greer, G. Focht, D. Turner and M. Freiman, "Gadolinium-Free Crohn's Disease Assessment from Magnetic Resonance Enterography Data," 2022 IEEE 19th International Symposium on Biomedical Imaging (ISBI), Kolkata, India, 2022, pp. 1-5, doi: 10.1109/ISBI52829. (Year: 2022).*

(Continued)

*Primary Examiner* — Delomia L Gilliard

(74) *Attorney, Agent, or Firm* — Dorsey & Whitney LLP

(57) ABSTRACT

A method of segmenting a bowel includes receiving patient imaging comprising one or more voxels; determining a lumen indicator based on the patient imaging; representing the one or more voxels within a distance of the lumen indicator as one or more feature vectors; generating, based on the one or more feature vectors, a cluster comprising at least one of the one or move voxels; binarizing the cluster into one or more groups based on a threshold value; and generating a bowel segment model based at least on the cluster.

19 Claims, 16 Drawing Sheets

(51) Int. Cl.

| | |
|---|---|
| ***A61B 5/055*** | (2006.01) |
| ***G06T 7/11*** | (2017.01) |
| ***G06T 7/136*** | (2017.01) |
| ***G16H 30/20*** | (2018.01) |
| ***G16H 50/50*** | (2018.01) |

(52) U.S. Cl.

CPC ............... *G06T 2207/10088* (2013.01); *G06T 2207/10132* (2013.01); *G06T 2207/20081* (2013.01); *G06T 2207/20092* (2013.01); *G06T 2207/30028* (2013.01)

(56) References Cited

U.S. PATENT DOCUMENTS

| | | | | |
|---|---|---|---|---|
| 12,165,241 | B1 * | 12/2024 | Meng | G06T 11/006 |
| 2003/0223627 | A1 * | 12/2003 | Yoshida | G06T 7/155 382/128 |
| 2016/0163048 | A1 * | 6/2016 | Yee | A61B 6/032 382/131 |
| 2016/0381256 | A1 * | 12/2016 | Aguirre-Valencia | H04N 13/30 348/46 |
| 2017/0098302 | A1 * | 4/2017 | Peters | G06T 7/0012 |
| 2018/0310907 | A1 * | 11/2018 | Zhang | G06F 3/0346 |
| 2020/0211189 | A1 * | 7/2020 | Yip | G06T 7/0012 |
| 2020/0261157 | A1 * | 8/2020 | Chen | A61B 34/20 |
| 2020/0265618 | A1 * | 8/2020 | Chen | G16H 50/50 |
| 2020/0279373 | A1 * | 9/2020 | Hussain | G16H 50/70 |
| 2020/0320688 | A1 * | 10/2020 | Tu | G06T 11/003 |
| 2021/0213304 | A1 * | 7/2021 | Domnik | G16H 30/40 |
| 2021/0264212 | A1 * | 8/2021 | Paik | G06N 3/09 |
| 2022/0330902 | A1 * | 10/2022 | Forneris | G16H 50/50 |
| 2024/0249409 | A1 * | 7/2024 | Mayer | G06N 3/0464 |
| 2024/0324852 | A1 * | 10/2024 | Bouhnik | A61B 34/25 |
| 2025/0315944 | A1 * | 10/2025 | Aben | G06T 7/66 |
| 2025/0375413 | A1 * | 12/2025 | Schmid-Schoenbein | A61K 31/365 |

OTHER PUBLICATIONS

Akilandeswari A, Sungeetha D, Joseph C, Thaiyalnayaki K, Baskaran K, Jothi Ramalingam R, Al-Lohedan H, Al-Dhayan DM, Karnan M, Meansbo Hadish K. Automatic Detection and Segmentation of Colorectal Cancer with Deep Residual Convolutional Neural Network. Evid Based Complement Alternat Med. Mar. 17, 2022 (Year: 2022).*

Yao Y, Gou S, Tian R, Zhang X, He S. Automated Classification and Segmentation in Colorectal Images Based on Self-Paced Transfer Network. Biomed Res Int. Jan. 20, 2021;2021:6683931. doi: 10.1155/2021/6683931. (Year: 2021).*

* cited by examiner

BOWEL SEGMENTATION SYSTEM AND METHODS

CROSS-REFERENCE TO RELATED APPLICATIONS

This application claims the benefit of priority under 35 U.S.C. § 119(c) and 37 C.F.R. § 1.78 to provisional application No. 63/489,363 filed on Mar. 9, 2023, titled "Semi-automated Segmentation of Inflamed Bowel Wall on Non-contrast T2-weighted MRI", and is related to provisional application No. 63/331,448 filed on Apr. 15, 2022, titled "System to Characterize Topology and Morphology of Fistulae from Medical Imaging Data", provisional application No. 63/447,910 filed on Feb. 24, 2023, titled "Virtual Examination System (vEUA)", and provisional application Ser. No. 18/135,019 filed on Apr. 14, 2023, titled "System to Characterize Topology and Morphology of Fistulae from Medical Imaging Data", all of which are hereby incorporated herein by reference in their entireties.

BACKGROUND

Crohn's disease is a chronic, auto-immune, inflammatory condition affecting the digestive tract. Crohn's disease affects approximately 300 out of every 100,000 people in Western Europe, causing a significant financial burden on healthcare systems. The available treatments are costly and have a high failure rate within the first year. Uncontrolled inflammation in the bowel can lead to significant damage, often requiring surgery for 10-30% of patients within five years of diagnosis.

Crohn's disease location and behavior is routinely assessed using magnetic resonance imaging (MRI) or magnetic resonance enterography (MRE) to evaluate the presence, extent, and activity of the disease. One important feature evaluated during MRE is the thickness of the bowel wall, which is strongly linked to the severity of the disease. There are limitations in bowel wall thickness measurement and it is believed that segmentation of abnormal bowel volume may facilitate more objective, quantitative assessment for tracking disease activity and treatment response. This is not feasible without automation due to constraints on clinicians time. Previous automated segmentation tools have used images acquired with Gadolinium contrast agents, which numerous studies suggest should be avoided.

Existing methods for assessing disease activity based on bowel wall thickness and other MRI features are considered time-consuming, limiting their clinical utility. Notably, changes in the length and volume of an abnormal segment of the bowel may provide more accurate information about the response to treatment compared to bowel wall thickness alone, which is valuable both for clinical use and drug development.

While some imaging techniques allow for automatic calculation of bowel wall thickness on certain MRI scans, reducing the need for manual input. Studies have used complex computer algorithms to automatically identify and measure abnormal bowel segments, achieving high accuracy and reproducibility. However, these previous studies have relied on contrast-enhanced imaging, which has raised concerns due to potential long-term health risks associated with the contrast agent used. In response to these concerns, there is a need for automated methods to analyze unenhanced structural imaging as part of routine MRE, ultimately reducing reliance on contrast-enhanced imaging and addressing associated safety concerns.

SUMMARY

In one embodiment, a method includes receiving, via a user interface, three-dimensional centerline input on a non-contrast T2-weighted magnetic resonance imaging (MRI) image and representing voxels within a threshold distance of the three-dimensional centerline as feature vectors. The method further includes generating clusters of the voxels using the feature vectors, binarizing the clusters into positive and negative groups of voxels based on a threshold value, and generating a segment of abnormal bowel within the noncontrast T2-weighted MRI image based at least on the binarized clusters.

In one embodiment, a method includes: receiving patient imaging including one or more voxels; determining a lumen indicator based on the patient imaging; representing the one or more voxels within a distance of the lumen indicator as one or more feature vectors; generating, based on the one or more feature vectors, a cluster including at least one of the one or move voxels; binarizing the cluster into one or more groups based on a threshold value; and generating a bowel segment model based at least on the cluster.

Optionally, in some embodiments, the one or more groups includes at least a positive group and a negative group; voxels in the positive group are included in the bowel segment model; and voxels in the negative group are excluded from the bowel segment model.

Optionally, in some embodiments, the bowel segment model represents a segment of abnormal bowel.

Optionally, in some embodiments, the patient imaging includes at least one of a magnetic resonance image (MRI), an ultrasound, or a computer tomography (CT) image.

Optionally, in some embodiments, the MRI includes a noncontrast T2-weighted MRI image.

Optionally, in some embodiments, the lumen indicator includes a three-dimensional centerline of the lumen.

Optionally, in some embodiments, the method further includes: receiving segmentation data; and evaluating the bowel segment model based on the segmentation data.

Optionally, in some embodiments, evaluating the bowel segment model includes at least one of comparing the bowel segment model to the segmentation data.

Optionally, in some embodiments, the comparison of the bowel segment model to the segmentation data includes at least one of a Dice score, a symmetric Hausdorff distance, a mean contour distance, a volume, or a length normalized volume.

Optionally, in some embodiments, the length normalized volume is based at least in part on a length of the lumen indicator.

Optionally, in some embodiments, the segmentation data includes manual segmentation data determined by a medical provider.

In one embodiment, a method for training an artificial intelligence (AI) model to segment portions of a bowel of a patient includes: receiving, by a processing element, patient imaging data associated with a lumen; receiving, by the processing element, a lumen indicator configured to mark a portion of the lumen; receiving, by the processing element, a segmentation data based on the lumen indicator, wherein the patient imaging data, the lumen indicator, and the segmentation data include training data; providing the training data to an artificial intelligence algorithm executed by the processing element; training, by the processing element, the artificial intelligence algorithm using the training data to learn a correlation between the lumen indicator and the segmentation data associated with the lumen within the patient imaging; determining, by the processing element, a bowel segment model based on the training data; and evaluating the bowel segment model based on a validation data.

Optionally, in some embodiments, the patient imaging includes one or more voxels, and determining the bowel segment model includes: representing the one or more voxels within a distance of the lumen indicator as one or more feature vectors; generating, based on the one or more feature vectors, a cluster including at least one of the one or move voxels; binarizing the cluster into one or more groups based on a threshold value; and generating a bowel segment model based at least on the cluster.

In one embodiment, a non-transitory computer-readable storage medium, the computer-readable storage medium including instructions that when executed by a processing element, cause the processing element to: receive patient imaging including one or more voxels; receive a lumen indicator based on the patient imaging; represent the one or more voxels within a distance of the lumen indicator as one or more feature vectors; generate, based on the one or more feature vectors, a cluster including at least one of the one or move voxels; binarizing the cluster into one or more groups based on a threshold value; and generate a bowel segment model based at least on the cluster.

Additional embodiments and features are set forth in part in the description that follows, and will become apparent to those skilled in the art upon examination of the specification and may be learned by the practice of the disclosed subject matter. A further understanding of the nature and advantages of the present disclosure may be realized by reference to the remaining portions of the specification and the drawings, which form a part of this disclosure. One of skill in the art will understand that each of the various aspects and features of the disclosure may advantageously be used separately in some instances, or in combination with other aspects and features of the disclosure in other instances.

DETAILED DESCRIPTION

Figure 1:
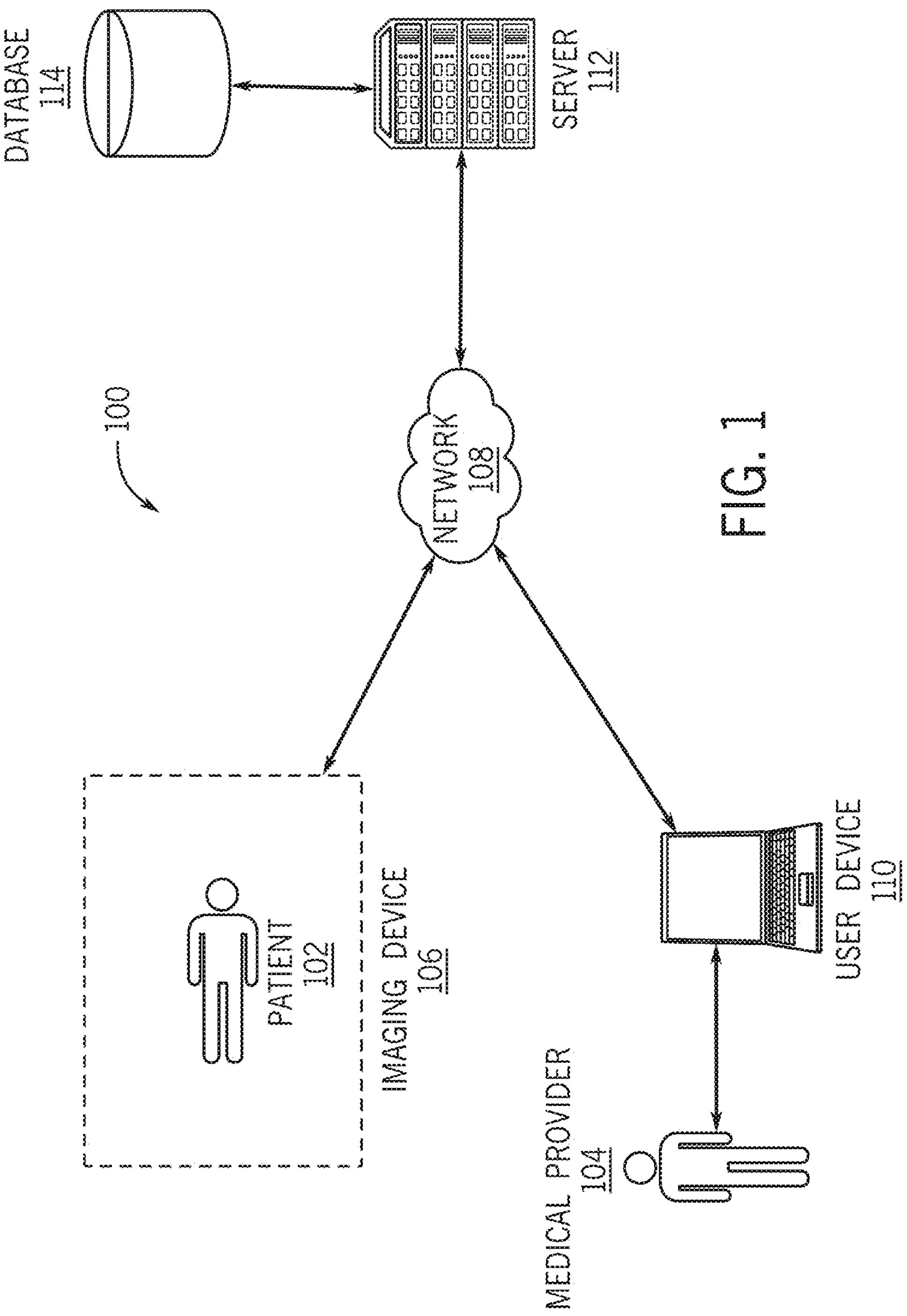
FIG. 1 is a schematic of an example of a bowel segmentation system.

Improved methods and systems of classifying or segmenting diseased and healthy portions of the bowel are disclosed. In various examples, the system captures imaging data of a patient's bowel, such as from an MRI scan, computer assisted tomography scan, ultrasound, x-ray, or the like. Given that full segmentation of Crohn's disease is prohibitively time-consuming for clinicians, the systems and methods disclosed herein take as input a one or more 3D lumen indicators (e.g., a centerline of an intestinal lumen) per abnormal bowel segment, and return a volumetric segmentation of the bowel. The system receives input from a user such as a medical provider or a technician indicating a centerline of a portion of the bowel. A user-drawn lumen indicator is generally rapid for a medical provider, such as a radiologist) to place and serves as a foundation for automated segmentation. The system uses the centerline to determine a three-dimensional representation of the bowel. The system segments the bowel into healthy and diseased portions. The term "bowel" refers to the long tube-like portion of the digestive tract that extends from the stomach to the anus. It includes the small intestine and the large intestine (colon), and may include interfaces with those structures as well, such as the ileum and terminal ileum.

In one example, a disclosed method includes, a segmentation protocol and semi-automated pipeline for use on coronal T2-weighted MRI, routinely acquired during Crohn's monitoring. Using a novel annotation protocol, expert radiologists may draw lumen indicators (e.g., 3D centerlines) through segments of abnormal bowel, and a volumetric segmentation of the wall was determined by the segmentation system 100 (see, e.g., FIG. 3B and FIG. 3C). The segmentation system may be trained, validated and tested on a modest dataset of patient imaging that may be divided into training, validation, and test sets.

In one example, a method for segmentation of abnormal bowel wall volume in Crohn's disease patients uses non-contrast T2 weighted images, commonly available in treatment records of Crohn's patients. The method can use real-world relatively low resolution data to develop an approach that may be generalizable to the clinical setting.

In one example, the method includes a bowel annotation protocol, creating ground truth data, a lumen indicator (e.g., lumen centerline) for a section of abnormal bowel, and corresponding segmentation of the surrounding intestinal wall. In one example, an artificial intelligence (AI) or machine learning (ML) algorithm takes a manually-created lumen indicator as input. A processing element performs unsupervised clustering to divide an image into small, contiguous clusters. Each cluster is characterized using a custom feature set, used as input to a random forest regressor, predicting the fraction of voxels in the bowel segment model. In some examples, the algorithm includes a neural network including convolutional layers and fully connected layers.

To validate the system, inter-reader agreement for two readers (e.g., medical providers 104 such as radiologists, physicians, or technicians) segmenting the bowel wall, based on the same centerline, may be quantified to verify that the output of the system agrees with humans at a level close to inter-reader agreement, with nonsignificant difference found when assessed using the Dice score and symmetric Hausdorff distance, but a significant difference seen with the mean contour distance. See e.g., FIG. 6A-6C and related discussion. The disclose methods of using the system may be included within a computer application such as a standalone program, web-based platform, or the like, further aid clinicians in deriving quantitative imaging biomarkers for the treatment of many inflammatory diseases including Crohn's disease.

In one example, the system may calculate a bowel wall thickness automatically with minimal user interaction on T1-weighted post contrast imaging. In addition, the system may include multi-stage, multi-scale feature extraction and classification models to perform fully-automated segmentation of abnormal bowel—in particular using support vector machines and random forests. In more examples, still, the method may add details of spatial context, and using active learning to reduce data requirements and time for model training. Such a method and system has achieved a Dice score of 0.924 on a detection task including the bowel lumen.

In statistics, specifically in the context of evaluating the performance of image segmentation or object detection algorithms, the Dice score, also known as the Sørensen-Dice coefficient, is a measure of the similarity or overlap between two sets of data. The Dice score may be used to assess the agreement between the predicted and ground truth segmentation masks or delincations obtained from medical imaging data, such as MRI or CT scans.

The mathematical formula for the Dice score is: [Dice={2|A∩B|/|A∪B| where:—|A| denotes the cardinality of set A (e.g., the number of pixels or voxels in the predicted segmentation mask)—|B| denotes the cardinality of set B (e.g., the number of pixels or voxels in the ground truth segmentation mask)—|A∩B| denotes the cardinality of the intersection of sets A and B (e.g., the number of overlapping pixels or voxels between the predicted and ground truth segmentation masks) The Dice score ranges from 0 to 1, where a score of 1 signifies good overlap between the predicted and ground truth masks (and generally a higher-quality model), while a score of 0 indicates no overlap (and generally a lower quality model). For example, the Dice score may be used to quantitatively assess the accuracy and performance of the segmentation algorithms and systems disclosed herein, providing a measure of how well the algorithm's predictions align with the ground truth segmentation, thereby informing the quality of the algorithm's performance in delineating structures or abnormalities within medical images.

In one such example the methods and systems disclosed herein used manual lumen indicators with region-growing and refinement based on active contours, using contrast-enhanced T1-weighted images, automatically extracting bowel wall volume and thickness measurements. In this example, even with independent manual lumen indicator inputs from multiple radiologists, the system increased reproducibility of extracted biomarker statistics relative to manual delineation. In another example, the system achieved segmentation of Crohn's lesions by combining manual lumen indicator input, curviplanar reformatting and deep learning using a 3D convolutional neural network (e.g., a U-net), achieving a Dice score of 0.75 for inflamed bowel wall.

The segmentation system 100 provides an efficient method of quantifying Crohn's disease burden, providing a novel, powerful tool for assessing disease severity and treatment response from routine clinical data. The benefits of the segmentation system 100 support proactive monitoring and precision management of patients and therapeutic development.

Turning to the figures, FIG. 1 illustrates an example of a segmentation system 100. In one example, the segmentation system 100 includes an imaging device 106 suitable to capture imaging studies of the gastrointestinal tract, including the colon, stomach, and small intestine of a patient 102. In some examples, the imaging device 106 may include one or more of an MRI, CT, ultrasound, x-ray, or the like.

The segmentation system 100 may include a user device 110 such as a desktop computer, laptop computer, smart phone, tablet, or other device suitable to enable a medical provider 104 to interact with the segmentation system 100.

The segmentation system 100 may include a server 112. The server 112 may have computational and/or storage capabilities greater than that of the user device 110. The server 112 may include or be in communication with a database 114 suitable to store medical imaging information from the imaging device 106, diagnostic information, medical records, and/or segmentation data developed by the segmentation system 100.

The devices of the segmentation system 100 may be in direct communication with one another, or may be in communication via a network 108. The network 108 may be implemented using one or more of various systems and protocols for communications between computing devices. In various embodiments, the network 108 or various portions of the network 108 may be implemented using the Internet, a local area network (LAN), a wide area network (WAN), and/or other networks. In addition to traditional data networking protocols, in some embodiments, data may be communicated according to protocols and/or standards including near field communication (NFC), Bluetooth, cellular connections, universal serial bus (USB), Wi-Fi, Zigbee, and the like.

Figure 2:
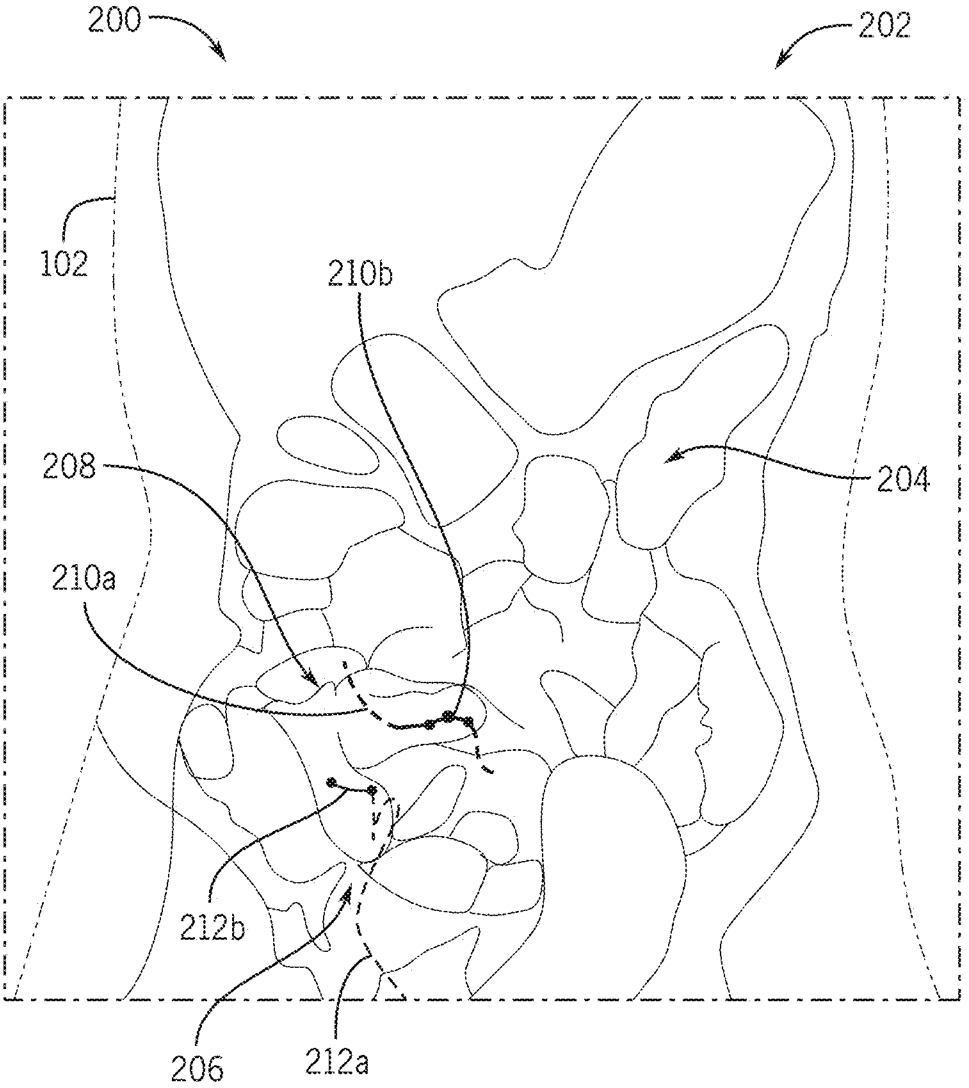
FIG. 2 is an example of patient imaging generated by the system of FIG. 1.

Turning to FIG. 2, an example of patient imaging 200 including ground truth data 202 generated or used by the segmentation system 100 is shown. The patient imaging 200 in this example is characteristic of an MRI image, but may be any other relevant imaging technology, such as ultrasound, CT, x-ray, or the like. The example patient imaging 200 shows a slice from a volumetric non-contrast T2-weighted image. This example patient imaging 200 shows disease segments for the terminal ileum 206 and ileum 208.

In the context of medical imaging AI/ML techniques, ground truth data may include authoritative or reference data that serves as the standard against which the performance of the segmentation system 100 is evaluated. This ground truth data 202 typically includes accurately annotated or labeled medical images, which have been reviewed and validated by medical providers 104 such as expert radiologists or practitioners. For example, these annotations may include delineations of relevant anatomical structures, such as the terminal ileum 206 and ileum 208 shown in FIG. 2. The ground truth data 202 may also identify abnormalities or lesions, or other clinically significant features within the medical images. The segmentation system 100 is trained to learn and recognize patterns, features, or abnormalities within the ground truth data 202. As discussed in more detail with respect to FIG. 5A-FIG. 7D, the accuracy and reliability of the segmentation system 100 may be assessed by comparing its output with the ground truth data.

Overlaid on the patient imaging 200, the ground truth data 202 may include one or more lumen indicators (e.g., lumen indicators 210*a* and/or lumen indicator 212*a*) intersecting the imaging plane. In the context of the human body, the term "lumen" refers to the inside space or cavity within a tubular structure such as a blood vessel, intestine, or other hollow organ. More broadly, it can also refer to the interior of any tubular structure within the body, such as the central space within a bronchus in the lungs or the space within the spinal cord. The lumen is the open space within a tubular structure through which air, fluid, or other substances can pass.

The segmentation system 100 may be trained, validated, and/or tested on an annotation protocol whose output is shown as shown in FIG. 2 and represented by a lumen indicator, such as the lumen indicator 210*a*, lumen indicator 212*a*, etc.

In the training method, a medical provider 104 such as an expert radiologist identified the coronal T2-weighted non-fat-saturated images. The medical provider 104 placed a lumen indicator (e.g., the lumen indicator 210*a* and/or lumen indicator 212*a*) through the lumen of an abnormal segment of small bowel. This training method is discussed in more detail with respect to FIG. 8A-FIG. 12. In one example, abnormal segments longer than 20 mm were considered, and terminal ileal disease was included proximal to the ileocaccal valve 906 (See FIG. 9A and FIG. 9B). The training method may include annotating abnormal segments of small bowel using unenhanced imaging. Traditional techniques typically used T1-weighted images, derived with a contrast or dye agent such as intravenous Gadolinium (IV Gad). Concerns about the use of IV Gad due to long-term retention of IV Gad in the brain have prompted guidelines to avoid use when not necessary. Thus, the disclosed training method can provide the benefit of advanced management of Crohn's disease without the deleterious effects of contrast agents. Thus, filling a clinical need for automated bowel wall segmentation from unenhanced structural imaging (e.g. T2-weighted), acquired as part of routine MRE. This training method was designed to standardize the identification and measurement of affected bowel segments to help ensure accurate and reliable analysis, to improve the assessment and monitoring of Crohn's disease using advanced imaging techniques, providing valuable insights for treatment decision-making and drug development.

In one example, to train the model, readers (e.g., medical providers 104) annotated training cases before being processed by the segmentation system 100 algorithm. Summary data of example training, testing, and validation datasets can be seen in Table 1 and 2

Main datasets (train/validation/test). Imaging data from patients with confirmed small bowel Crohn's disease were collected from six different hospitals (see Table 1). Abnormal bowel segments, identified based on pre-existing clinical information, had lumen indicators drawn by medical providers 104 such as expert radiologists (segmentation was performed based on these by a technician or radiologist). The technicians could consult for lumen indicators clarification, and modify their segmentations accordingly. Data were checked for consistency with the protocol by an experienced researcher and expert radiologist before signoff. See FIGS. 10-12 and related discussion for details of this method 1000.

TABLE 1

Training, testing and validation dataset summary

| | | Dataset TRAIN | TEST | VALIDATION | Total |
|---|---|---|---|---|---|
| Group | Newly diagnosed | 27 (55%) | 20 (59%) | 10 (56%) | 57 (56%) |
| | Suspected relapse | 20 (41%) | 14 (41%) | 7 (39%) | 41 (41%) |
| | Not known | 2 (4%) | 0 (0%) | 1 (6%) | 3 (3%) |
| | Total | 49 (49%) | 34 (34%) | 18 (18%) | 101 (100%) |
| Site | A | 8 (17%) | 0 (0%) | 2 (11%) | 10 (10%) |
| | B | 3 (6%) | 0 (0%) | 0 (0%) | 3 (3%) |
| | C | 2 (4%) | 6 (19%) | 2 (11%) | 10 (10%) |
| | D | 4 (8%) | 1 (3%) | 3 (17%) | 8 (8%) |
| | E | 3 (6%) | 3 (9%) | 2 (11%) | 8 (8%) |
| | F | 28 (58%) | 22 (69%) | 9 (50%) | 59 (60%) |
| | NA | 1 | 2 | 0 | 3 |
| | Total | 49 (49%) | 34 (34%) | 18 (18%) | 101 (100%) |
| Sex | Female | 31 (63%) | 15 (44%) | 11 (61%) | 57 (56%) |
| | Male | 18 (37%) | 19 (56%) | 7 (39%) | 44 (44%) |
| | Total | 49 (49%) | 34 (34%) | 18 (18%) | 101 (100%) |

TABLE 1-continued

Training, testing and validation dataset summary

| | | Dataset TRAIN | TEST | VALIDATION | Total |
|---|---|---|---|---|---|
| Age group | >40 | 1 (2%) | 0 (0%) | 0 (0%) | 1 (1%) |
| | >45 | 4 (8%) | 5 (15%) | 5 (28%) | 14 (14%) |
| | 16-25 | 26 (53%) | 14 (41%) | 9 (50%) | 49 (49%) |
| | 26-35 | 10 (20%) | 9 (26%) | 2 (11%) | 21 (21%) |
| | 36-45 | 8 (16%) | 6 (18%) | 2 (11%) | 16 (16%) |
| | Total | 49 (49%) | 34 (34%) | 18 (18%) | 101 (100%) |
| Montreal A | A1 | 6 (12%) | 8 (24%) | 3 (17%) | 17 (17%) |
| | A2 | 32 (65%) | 16 (47%) | 10 (56%) | 58 (57%) |
| | A3 | 4 (8%) | 4 (12%) | 0 (0%) | 8 (8%) |
| | Not known | 7 (14%) | 6 (18%) | 5 (28%) | 18 (18%) |
| | Total | 49 (49%) | 34 (34%) | 18 (18%) | 101 (100%) |
| Montreal L | L1 | 8 (16%) | 6 (18%) | 4 (22%) | 18 (18%) |
| | L2 | 1 (2%) | 0 (0%) | 1 (6%) | 2 (2%) |
| | L3 | 11 (22%) | 8 (24%) | 2 (11%) | 21 (21%) |
| | Not known | 29 (59%) | 20 (59%) | 11 (61%) | 60 (59%) |
| | Total | 49 (49%) | 34 (34%) | 18 (18%) | 101 (100%) |
| Montreal B | B1 | 24 (49%) | 17 (50%) | 10 (56%) | 51 (50%) |
| | B2 | 13 (27%) | 8 (24%) | 2 (11%) | 23 (23%) |
| | B3 | 5 (10%) | 3 (9%) | 1 (6%) | 9 (9%) |
| | Not known | 7 (14%) | 6 (18%) | 5 (28%) | 18 (18%) |
| | Total | 49 (49%) | 34 (34%) | 18 (18%) | 101 (100%) |
| Current treatment | No | 31 (63%) | 14 (41%) | 12 (67%) | 57 (56%) |
| | Yes | 17 (35%) | 18 (53%) | 6 (33%) | 41 (41%) |
| | Not known | 1 (2%) | 2 (6%) | 0 (0%) | 3 (3%) |
| | Total | 49 (49%) | 34 (34%) | 18 (18%) | 101 (100%) |
| Number of SB segments | 1 | 44 (90%) | 31 (91%) | 16 (89%) | 91 (90%) |
| | 2 | 2 (4%) | 3 (9%) | 2 (11%) | 7 (7%) |
| | 3 | 1 (2%) | 0 (0%) | 0 (0%) | 1 (1%) |
| | 4 | 1 (2%) | 0 (0%) | 0 (0%) | 1 (1%) |
| | 5 | 1 (2%) | 0 (0%) | 0 (0%) | 1 (1%) |
| | Total | 49 (49%) | 34 (34%) | 18 (18%) | 101 (100%) |

Table S, below, shows demographic information for inter-reader datasets.

TABLE 2 demographic information for inter-reader datasets

| | | Dataset INTER-READER |
|---|---|---|
| Sex | Male | 12 (33%) |
| | Female | 24 (67%) |
| Age group | 16-25 | 12 (33%) |
| | 26-35 | 17 (47%) |
| | 36-45 | 3 (8%) |
| | >45 | 4 (11%) |
| Montreal A | A1 | 11 (31%) |
| | A2 | 23 (64%) |
| | A3 | 2 (6%) |
| Montreal L | L1 | 5 (14%) |
| | L2 | 6 (17%) |
| | L3 | 25 (69%) |
| Montreal B | B1 | 24 (67%) |
| | B2 | 6 (17%) |
| | B3 | 6 (17%) |
| Current treatment | No | 10 (28%) |
| | Yes | 26 (72%) |
| Previous surgery | None | 26 (72%) |
| | Right hemicolectomy | 4 (11%) |
| | Ileocolonic resection | 6 (17%) |

In one example, patients 102 were randomly split to training, validation, and testing data sets. The training set (60 segments, 49 patients) was used for explicit optimization (parameter fitting). The validation set (20 segments, 18 patients) was used for interim performance quantification (and thus algorithm optimization) of the whole pipeline or its constituent parts. The test set (37 segments, 34 patients) was held out for the entire development.

In one example, to correctly examine inter-reader agreement of lumen indicator (e.g., centerline) based segmentation, readers worked from the same lumen indicator. Eighteen cases from the an example dataset (see table S2) were annotated on coronal T2-weighted non-contrast MRI, with centerlines drawn through the terminal ileum 206 by a first reader, which were then independently segmented by the first reader and a second reader in isolation from one another.

Figure 3A:
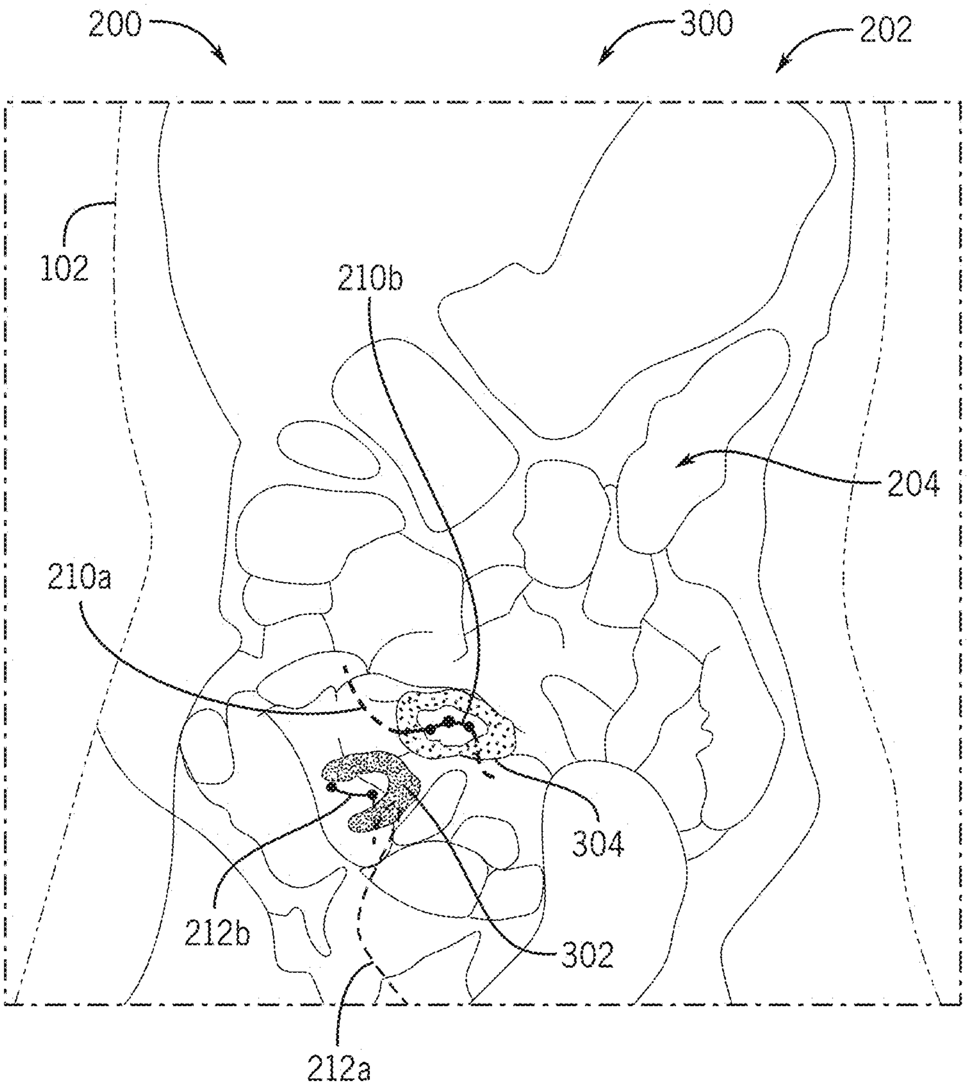
FIG. 3A is an example of a bowel segment model generated by the system of FIG. 1 including a lumen indicator of segments of the bowel.

Turning to FIG. 3A, the same image as FIG. 2, with an example of ground truth data 202 with system output 300 overlaid thereon. Lumen indicator 210*a*, marked portion 210*b*, lumen indicator 212*a*. marked portion 212*b* are shown alongside bowel segment model 302 and bowel segment model 304 encompassing out-of-plane segmented voxels.

In the context of medical imaging, a voxel may refer to a three-dimensional (3D) pixel, which is the basic unit of volume in an image dataset obtained through techniques such as computed tomography (CT), magnetic resonance imaging (MRI), or other 3D medical imaging modalities. A voxel may represent a data point within a 3D grid that defines the spatial characteristics of the imaged anatomy. Each voxel encapsulates information about a small volume element within the scanned region, and it is characterized by its position in 3D space as well as the intensity or density of the tissue or material it represents. Voxels serve as the building blocks of the 3D image, allowing the visualization and analysis of anatomical structures and pathological findings with spatial detail. The segmentation system 100 may analyze voxels within a medical image to enable assessment of tissue properties, the identification of abnormalities, and the visualization of anatomical structures in a fine-grained and volumetric manner. For example the segmentation system 100 may process and analyze image data at the voxel level to extract features, segment structures, or classify pathologies, thereby leveraging the 3D information contained within the voxel grid for comprehensive and detailed image interpretation.

Figure 3B:
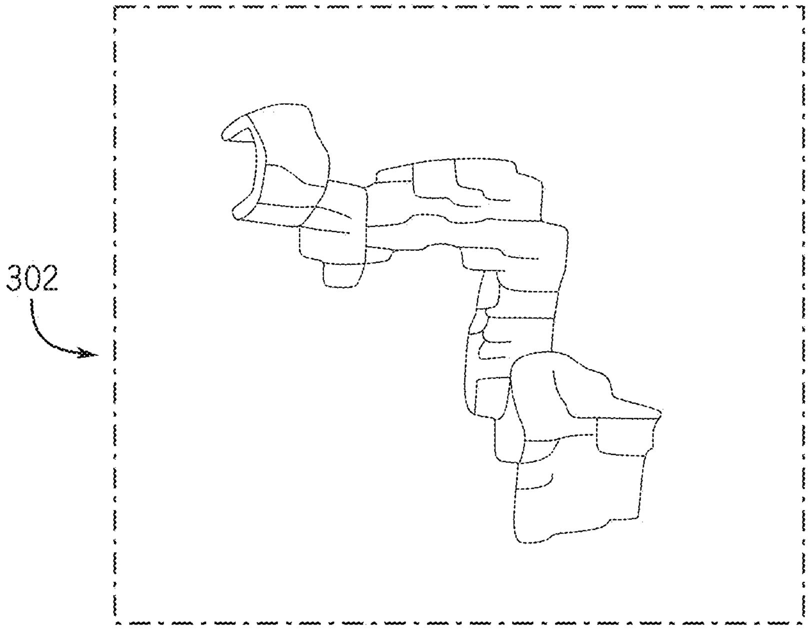
FIG. 3B is an example of bowel segment model including a three dimensional representation of a diseased portion of a bowel, generated by the system of FIG. 1.
Figure 3C:
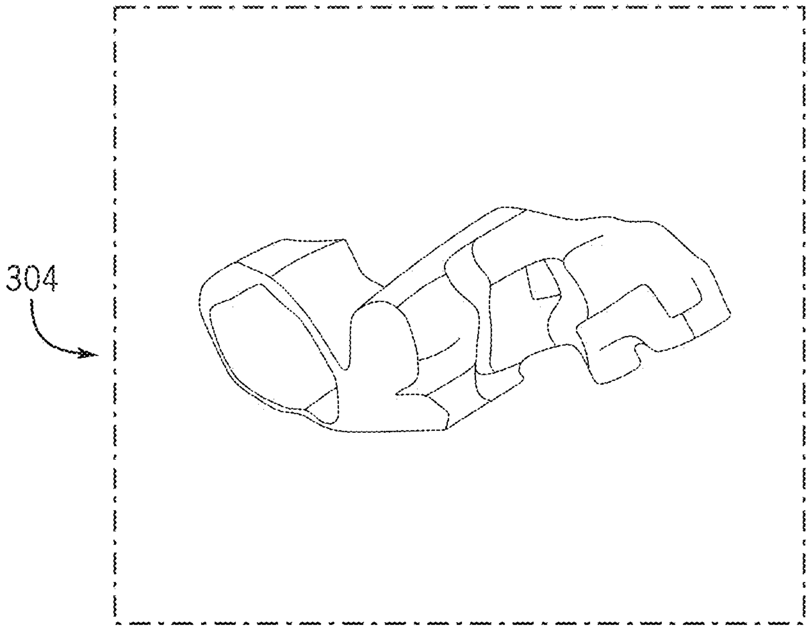
FIG. 3C is an example of bowel segment model, a three dimensional representation of a diseased portion of a bowel, generated by the system of FIG. 1.

Ground truth data 202 is shown including examples of a bowel segment model 302 and a bowel segment model 304, based respectively on the lumen indicator 210*a*, marked portion 210*b*, lumen indicator 212*a*, and marked portion 212*b* as previously discussed. The bowel segment model 302 and the bowel segment model 304 may be three-dimensional models of segments or portions of the bowel of the patient 102 as determined by the segmentation system 100 and the methods disclosed herein. FIG. 3B and FIG. 3B show detailed views of the bowel segment model 302 and the bowel segment model 304. The bowel segment model 302 and bowel segment model 304 may be used by a medical provider 104 to locate and treat diseased sections of the bowel 204, such as with drugs, surgery, or other medical interventions, while leaving healthy portions of the bowel 204 alone. Additionally, or alternately, the medical provider 104 may use bowel segment models developed over time to gauge the efficacy of treatments, such as drugs, diet, exercise and lifestyle changes. For example the medical provider 104 may compare the volume, length, extent, thickness, or other aspects of a bowel segment model 302 or a bowel segment model 304 at an initial time and prescribe a course of treatment. The medical provider 104 may re-assess the bowel segment model 302 and/or bowel segment model 304 at a later time, e.g., after treatment using the system 100. The medical provider 104 may compare the same, or similar, aspects of the bowel segment model 302 or the bowel segment model 304 determined after treatment with those before treatment, and may decide to continue, stop, or change the treatment, prescribe surgery or take other suitable action. Thus, the patient 102 may have better outcomes and disease management than with traditional approaches.

Turning to FIG. 4A-FIG. 4D, example outputs of steps of the method 1000 are shown.

Figure 4A:
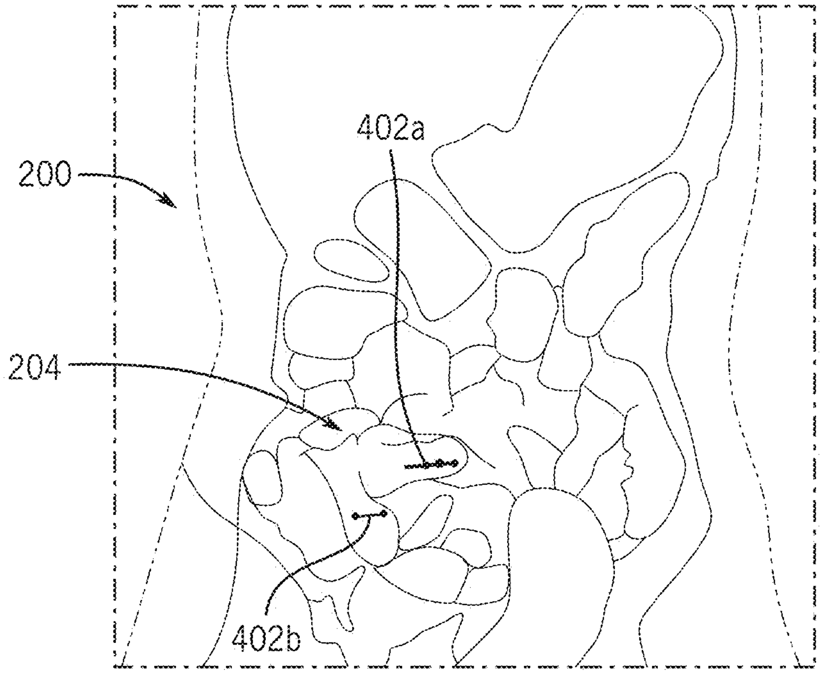
FIG. 4A is an example output of a step of generating a bowel segment model via the system of FIG. 1, including two-dimensional projections of a lumen indicator of a diseased portion of the bowel.
Figure 4B:
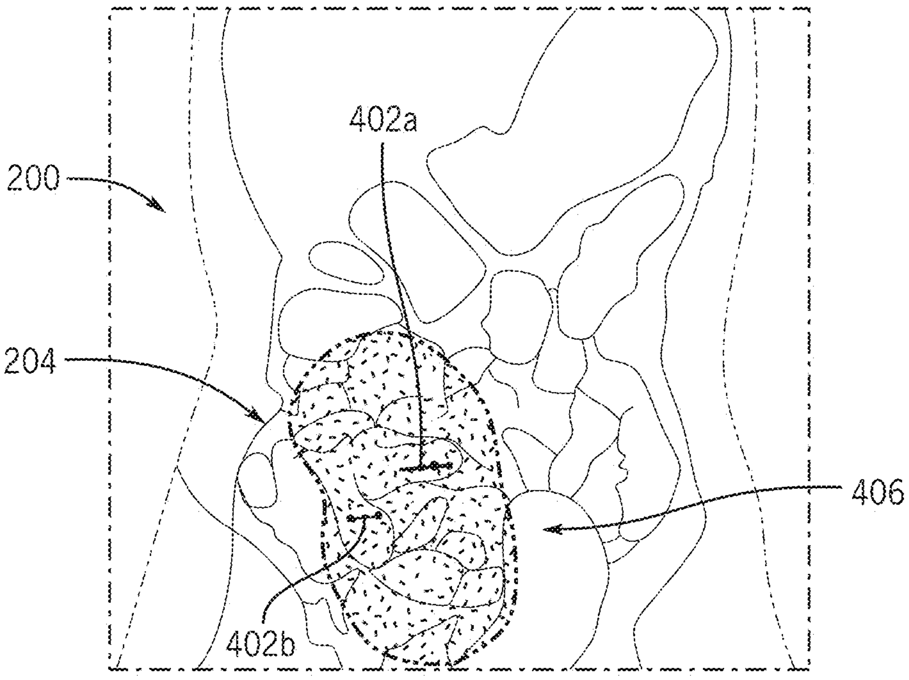
FIG. 4B is an example output of a step of generating a bowel segment model via the system of FIG. 1, including clustering about the lumen indicator.
Figure 4C:
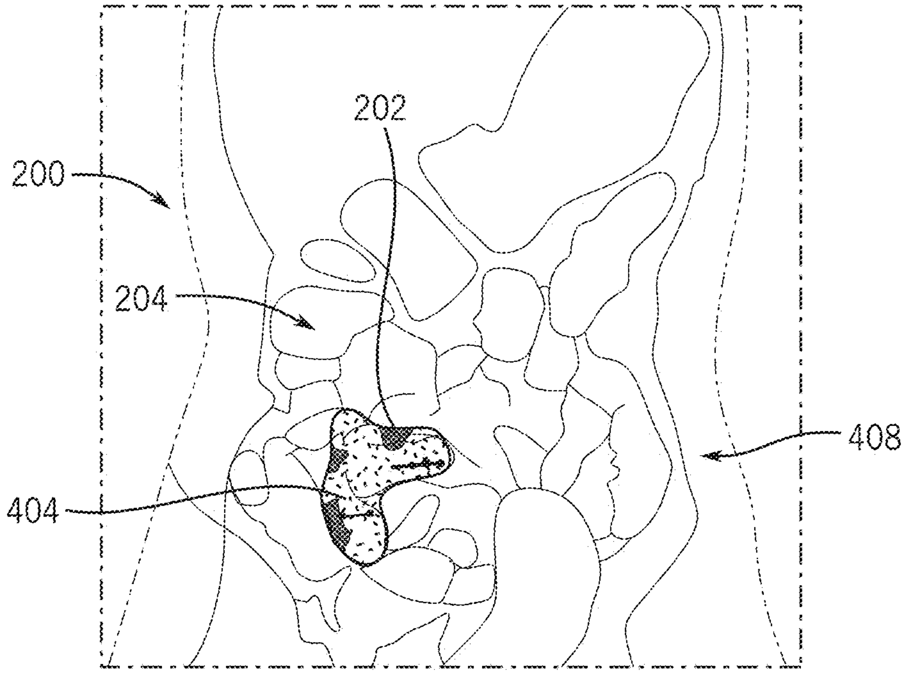
FIG. 4C is an example output of a step of generating a bowel segment model via the system of FIG. 1, including ground truth data and a bowel segment model.
Figure 4D:
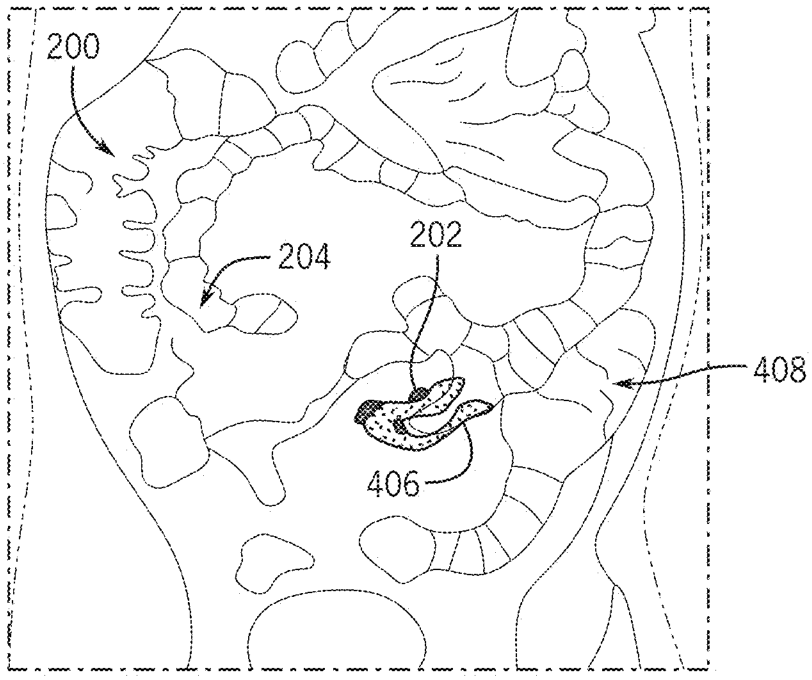
FIG. 4D is an example output of a step of generating a bowel segment model via the system of FIG. 1, including ground truth data and a bowel segment model

In some examples, e.g., shown in FIG. 4A, an input/source image includes 2D projections (e.g., two-dimensional projection 402*a* and/or two-dimensional projection 402*b*) of one or more lumen indicators (e.g., lumen indicator 210*a*, and lumen indicator 212*a*). As shown for example in FIG. 4B, one or more clusters 404, 406 are generated from the respective lumen indicator 210*a*, lumen indicator 210. FIG. 4C shows examples of algorithmic output 408 and ground truth data 202, e.g., from an anterior view. FIG. 4D shows the example of FIG. 4C from another point of view (e.g., a lateral view).

In some examples of clustering calculations shown for example in FIG. 4A, each coronal plane image is bilaterally filtered (e.g., 7×7 kernel, $\sigma$=75 for spatial and intensity dimensions), and voxel intensities scaled by a factor of (e.g., 0.08). Each voxel within a threshold (e.g., 50-mm of the lumen indicator is represented as a 4-D feature vector, including: the in-plane coordinates of the voxel (e.g., in mm), the minimum distance from the voxel to the lumen indicator (e.g., in mm), and the intensity of the voxel in the bilaterally filtered/rescaled image. The distance threshold may vary as desired. For example, the distance threshold may 0 mm (e.g., if a portion of the lumen indicator overlaps with a portion of the bowel 204 wall), 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18, mm, 19 mm, 20 mm, or longer (e.g., up to and including 50 mm), or larger. The number of voxels clustered is termed nv. Clustering is performed using k-means, with $k=10\sqrt{nv}$. See examples in FIG. 4A.

In some examples, each cluster 404, 406 is described by a vector of the following hyperparameters. Fifteen features originate from three sets of values based on the voxels in the cluster: raw voxel intensities; intensity after filtering with a Laplacian-of-Gaussian filter, kernel size (e.g., 2 mm); and 3D distance between each cluster 404,406 voxel and lumen indicator; and minimum, maximum, range, standard deviation, mean for each. Features may further include minimum 3D distance of the cluster 404, cluster 406 centroid from the respective lumen indicator 210*a*, lumen indicator 212*a*; difference between mean intensity of the cluster 404, 406 voxels, and the voxels surrounding the closest point where the respective lumen indicator intersects the current imaging plane; the minimum distance, in the direction orthogonal to the coronal plane, between the cluster 404, 406 and the lumen indicator 210*a*, lumen indicator 212*a*; the difference between mean of voxel intensities, and the mean of the voxel intensities within a threshold (e.g., three connected voxels (in-plane). In some examples, the feature vectors for each cluster 404, cluster 406 are fed to a random forest regression model executed by a processing element of the segmentation system 100. The regressor may be trained as follows: training and validation sets may be used to generate clusters 404, 406 as described herein, and the degree of overlap with the ground truth data 202 quantified (e.g., the fraction of voxels within the cluster 404, 406 which were segmented in the ground truth data 202). A random forest regressor may be trained to predict this fraction based on the feature vector, for the training set. Modifications to the feature set, pipeline and hyperparameters may be based on results for the validation set.

In some examples, to decide whether a cluster's constituent voxels are included in the final segmentation, a threshold is applied to the continuous predictions from the regressor. In some examples, the threshold is set at 0.35, selected by examining the mean Dice score that would result from different values on the validation set (see, e.g., FIG. 5A and related discussion).

In some examples, system output 300 may be subject to post-processing. For example, the union of included clusters for each coronal slice may be median-filtered (e.g., 3×3 kernel). The voxel count of each contiguous region of voxels may be calculated, and any region with a count below a threshold (e.g., 33% of the maximum) may be removed.

Figure 5B:
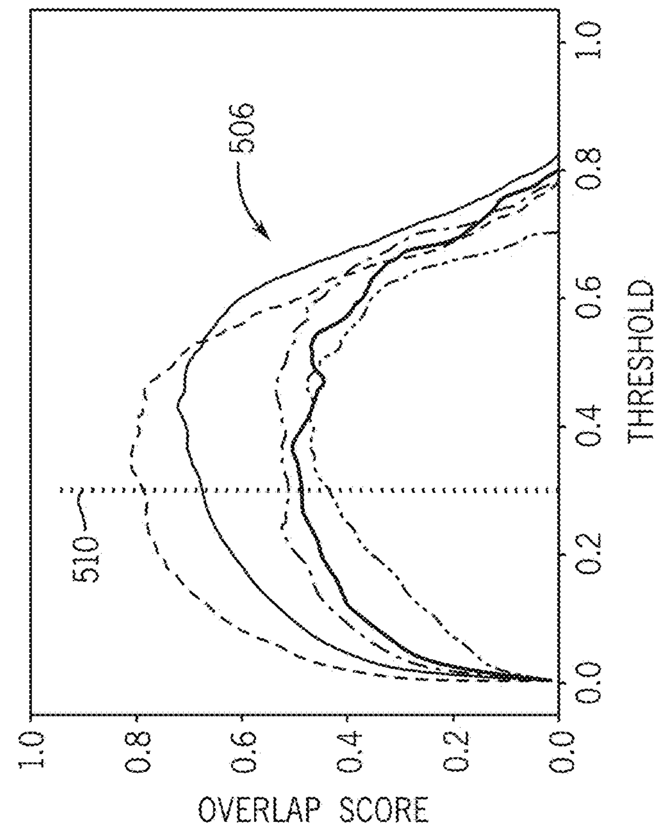
FIG. 5B illustrates threshold selection for binarizing voxels in patient imaging, of the system of FIG. 1.
Figure 5A:
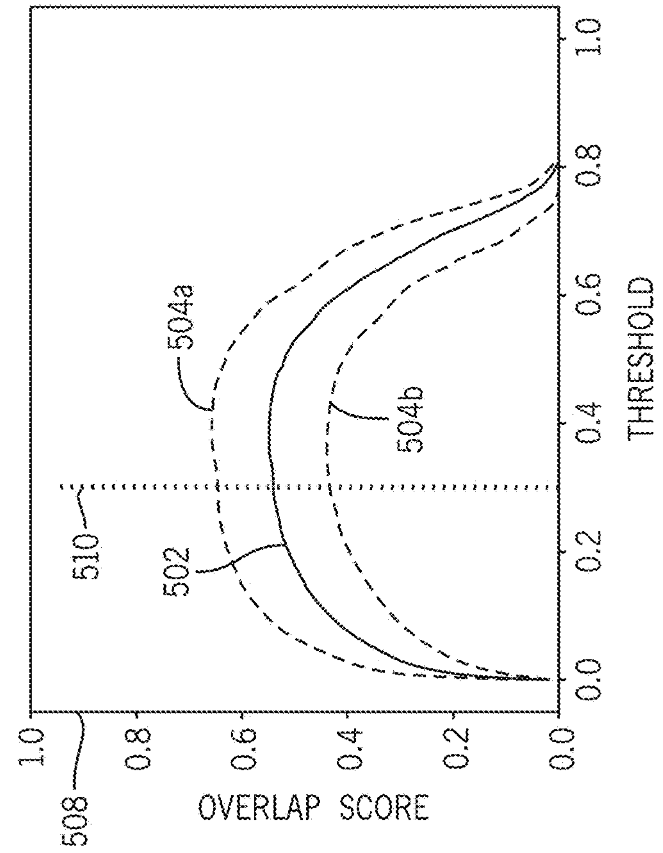
FIG. 5A illustrates threshold selection for binarizing voxels in patient imaging, of the system of FIG. 1.

FIG. 5A and FIG. 5B illustrates a threshold selection method for binarizing continuous predictions in the validation set. As used herein, "binarizing" may refer to a process of converting an input image (e.g., a patient imaging 200) into a binary image. In one example, the patient imaging 200 is binarized through a process of thresholding. For example, the segmentation system 100 may segment the bowel 204 by thresholding continuous outputs of a regression model. In some examples, to decide whether a cluster's constituent voxels are included in the final segmentation, a threshold 510 is applied to the continuous predictions from the regressor. For example, the threshold 510 may be set at set at 0.35, as shown for example in FIG. 5A and FIG. 5B selected by examining the mean Dice score that would result from different values on the validation set (see FIG. 5A and FIG. 5B). Other values of the threshold 510 may be selected as desired, e.g., based on different medical conditions that the bowel is being segmented to detect, different patient traits, etc. For example, the threshold 510 may be 0, 0.1, 0.2, 0.3, 0.4, 0.5, 0.6, 0.7, 0.8, 0.9, 1, or values therebetween. As discussed with respect to FIG. 6A-FIG. 6C a single threshold may not be not optimal for all datasets. Therefore, in some embodiments, an adaptive threshold selection method may be used. In other embodiments, a manual user-driven adjustment to thresholding may be used.

For example, as shown in FIG. 5A, binarizing may be achieved by applying one or more thresholds to the data of the patient imaging 200 (e.g., to each pixel of each slice of an MRI), or to each voxel in the case of a 3D image, which sets a certain intensity level as the dividing criterion between included and excluded pixels or voxels.

In the example shown in FIG. 5A and FIG. 5B, to select a threshold for binarizing clusters into positive and negative groups of voxels, the influence of the threshold value on an overlap score (e.g., the Dice score) may be evaluated. For example, the Dice score may be calculated on a scale from 0 to 1. Voxels meeting a certain threshold 510 may be included in the bowel segment model (e.g., the bowel segment model 302 or the bowel segment model 304), while those falling below a threshold 510 may be excluded. FIG. 5A shows an example of the mean 502 overlap score 508 vs. threshold 510, and an upper standard deviation 504*a* and lower standard deviation 504*b* about that mean 502. FIG. 5B shows the same data as FIG. 5A, but for individual lumen indicator/bowel segment model pair samples 506.

Figure 6A:
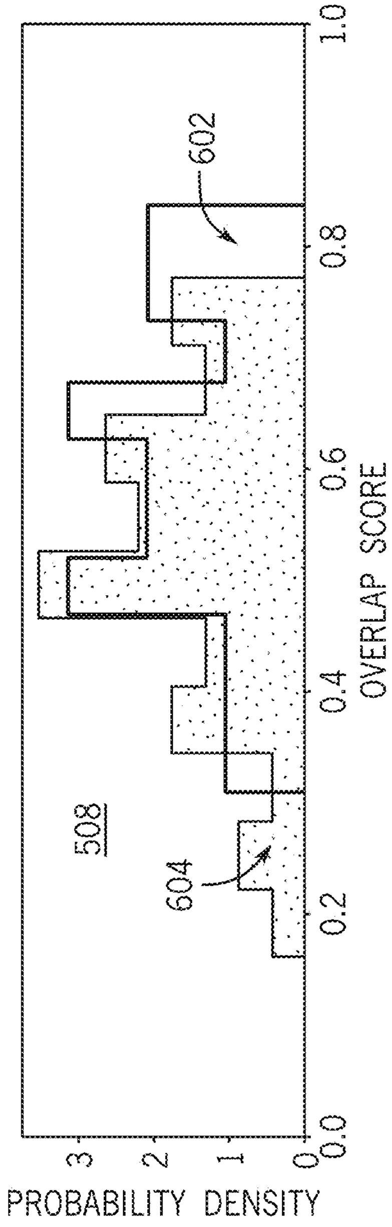
FIG. 6A-FIG. 6C illustrate histograms of segmentation metrics for inter-reader agreement and algorithm versus human, based on a test set, for the system of FIG. 1.
Figure 6B:
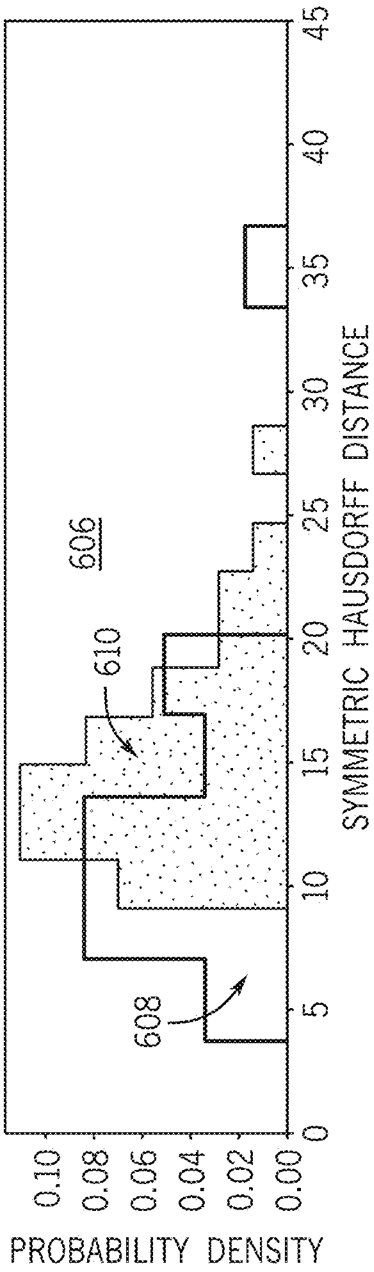
Figure 6C:
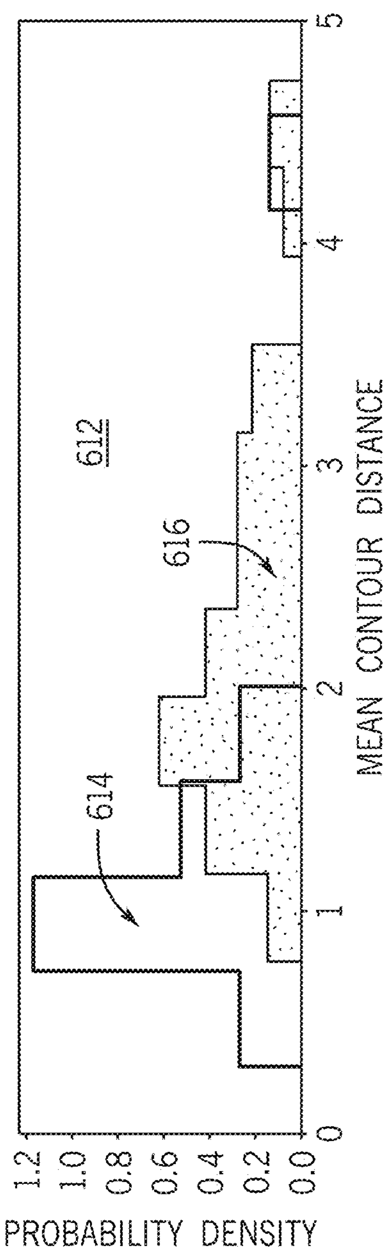

FIG. 6A, FIG. 6B, and FIG. 6C shows examples of histograms comparing inter-reader agreement and human v. segmentation system 100 performance for three example metrics, based on the test set of patient imaging 200. Algorithmic performance may be compared against inter-reader agreement, for segmentations based on the same lumen indicator. FIG. 6A—FIG. 6C show examples of this agreement, in addition to agreement of the output of the segmentation system 100 with human readers. As discussed herein, the mean overlap (e.g., Dice score) for inter-reader agreement is 0.603 in one example; for the algorithm on the test set it is 0.521 in one example. This difference is statistically insignificant using a two-sample Kolmogorov-Smirnov test. Likewise, the difference in the Symmetric Hausdorff distance 606 is not statistically significant. However, a difference in distribution is detectable for mean contour distance 612. In some examples, a mean contour distance may represent (e.g., the average distance between the outlines of two shapes, e.g., two bowel segment models). Agreement of the output of the segmentation system 100 with experts is statistically-equivalent as quantified by Dice (see, e.g., FIG. 6A) or Symmetric Hausdorff distance 606 (see, e.g., FIG. 6B), but worse when quantified by Mean Contour Distance (Sec, e.g., FIG. 6C). While a Dice coefficient of 0.52 may appear low, reproducible segmentation of the bowel wall is challenging: e.g., in one example inter-reader agreement gives a Dice score of 0.6.

FIG. 6A shows an example probability density and overlap score 508 (e.g., Dice score) for both inter-reader comparison and human v. segmentation system 100. As shown in FIG. 6A, the inter-reader agreement overlap score probability density 602 and the algorithm v. human overlap score probability density 604 have a high degree of correlation, indicating that the segmentation system 100 is consistent with expert readers at determining overlap (or Dice) score. For example, a statistically significant difference in overlap scores 508 cannot be detected. In the example shown, the Kolmogorov-Smirnov (K-S) statistic may be calculated. The K-S statistic is a value that quantifies the discrepancy between an empirical distribution of data and a reference distribution (e.g., a theoretical distribution or a second empirical distribution). In FIG. 6A, the (K-S statistic=0.285, p=0.230) for the inter-reader agreement overlap score probability density 602 and algorithm v. human overlap score probability density 604.

FIG. 6B shows an example probability density and Symmetric Hausdorff distance 606 for both inter-reader comparison and human v. segmentation system 100. The symmetric Hausdorff distance may be used to measure the dissimilarity between two spatial point sets, providing a probabilistic representation of the variability in their spatial relationships. This metric may be calculated by considering the maximum distance from each point in one set to its nearest point in the other set, and then taking the average or probability density of these distances. The resulting value provides insight into the degree of similarity or dissimilarity between the two point sets, with an emphasis on their spatial distribution. As shown in FIG. 6B, the inter-reader agreement symmetric Haudsorff distance probability density 608 and algorithm v. human symmetric Haudsorff distance probability density 610 also show a high degree of correlation between the human vs. segmentation system 100 and inter-reader comparison. In the example shown, a difference in Symmetric Hausdorff distance 606 cannot be detected (K-S statistic=0.339, p=0.099).

FIG. 6C shows an example probability density and mean contour distance 612 for both inter-reader comparison and human v. segmentation system 100. As shown in FIG. 6C, the inter-reader agreement mean contour distance probability density 614 and the algorithm v. human mean contour distance probability density 616 also show a degree of correlation, but lesser than in FIG. 6B and FIG. 6C. For example, differences in the mean contour distance 612 can be detected (K-S statistic=0.697, $p=4.51\times10^{-6}$).

Each of FIG. 6A-FIG. 6C show that the segmentation system 100 may be beneficially used to segment the bowel similar to how expert readers would, but with a higher degree of reproducibility and accuracy, and with much less time and effort invested. Because manual segmentation can only be practiced reliably by very few, specially-trained medical providers 104, the procedure is essentially out of reach for most patients. Therefore, the segmentation system 100 provides a capability and benefit to patients 102 that they previously could not enjoy.

Figure 7A:
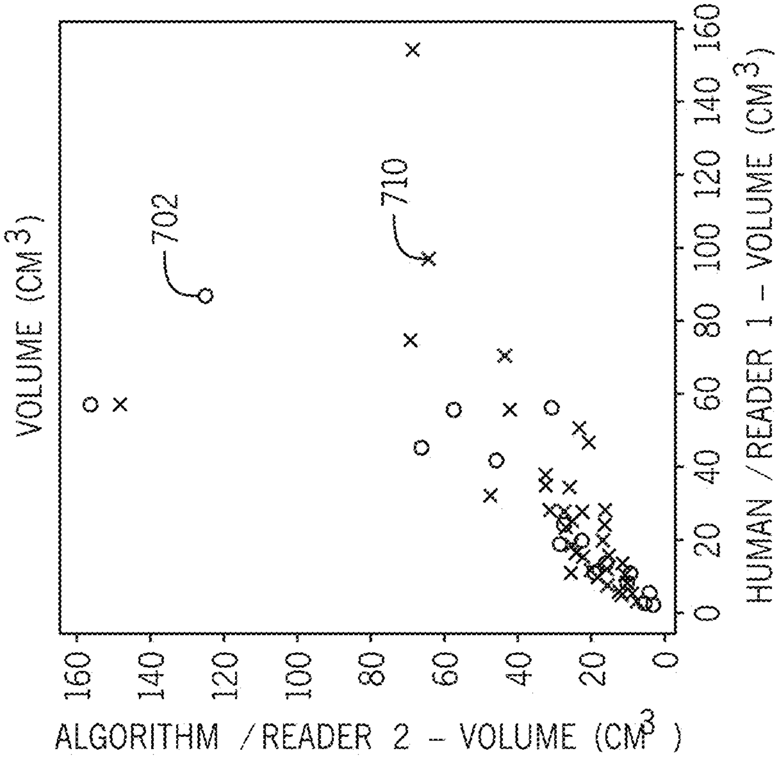
FIG. 7A illustrates inter-reader agreement and algorithm v. human performance for segmentation volumes, for the system of FIG. 1.
Figure 7B:
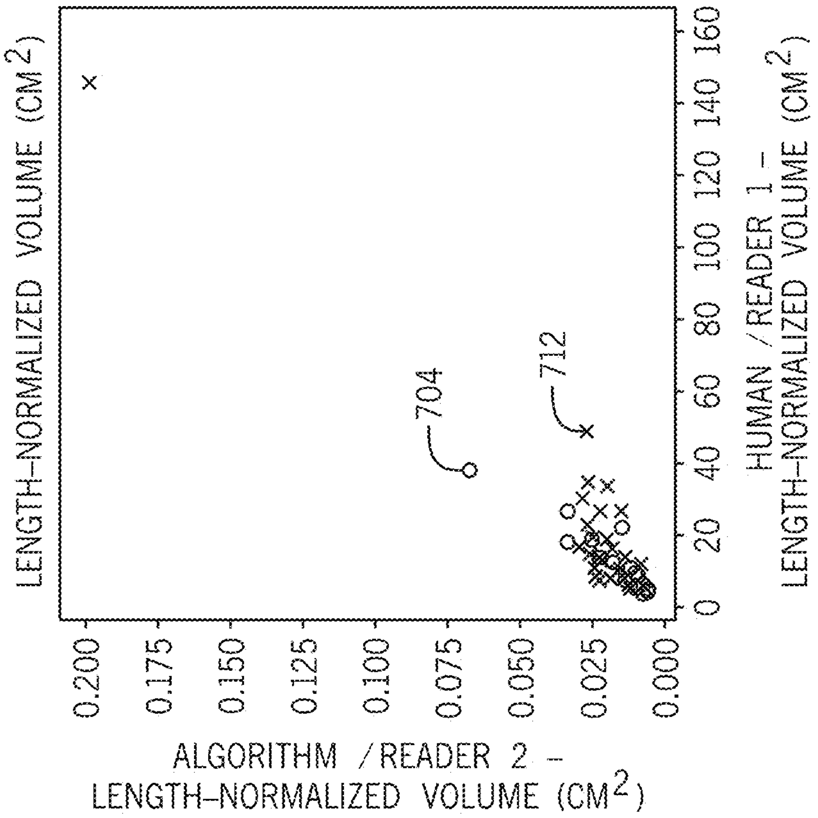
FIG. 7B illustrates inter-reader agreement and algorithm v. human performance for length-normalized segmentation volumes, for the system of FIG. 1.
Figure 7D:
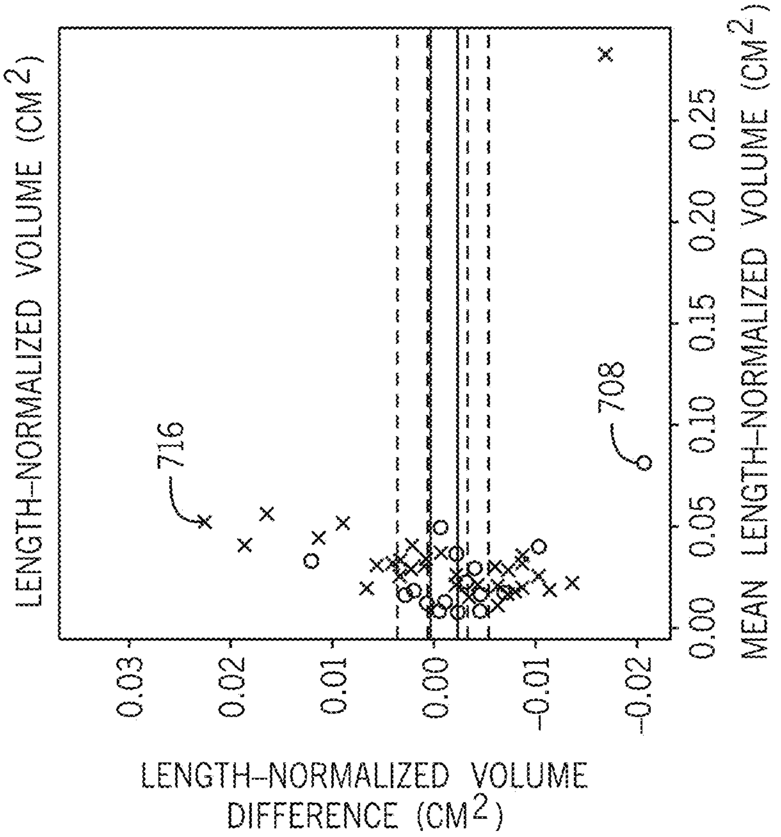
FIG. 7D illustrates volume difference for inter-reader and algorithm v. human performance for length-normalized segmentation volume, for the system of FIG. 1.

FIG. 7A-FIG. 7D show additional examples of the levels of agreement for two summary statistics, total segmented volume ($cm^3$ see, e.g., FIG. 7A and FIG. 7C) and volume-per-unit-length ($cm^2$ see FIG. 7B and FIG. 7D). Bland-Altman analysis detects no systematic bias between readers or algorithm and reader-95% confidence intervals intersect 0 for both summary statistics. FIG. 7A shows an inter-reader volume measurement 702 compared to an algorithm v. human volume measurement 710. FIG. 7D shows an inter-reader mean difference of length normalized volume measurement 708 compared to an algorithm v. human difference of length normalized volume measurement 716.

Figure 7C:
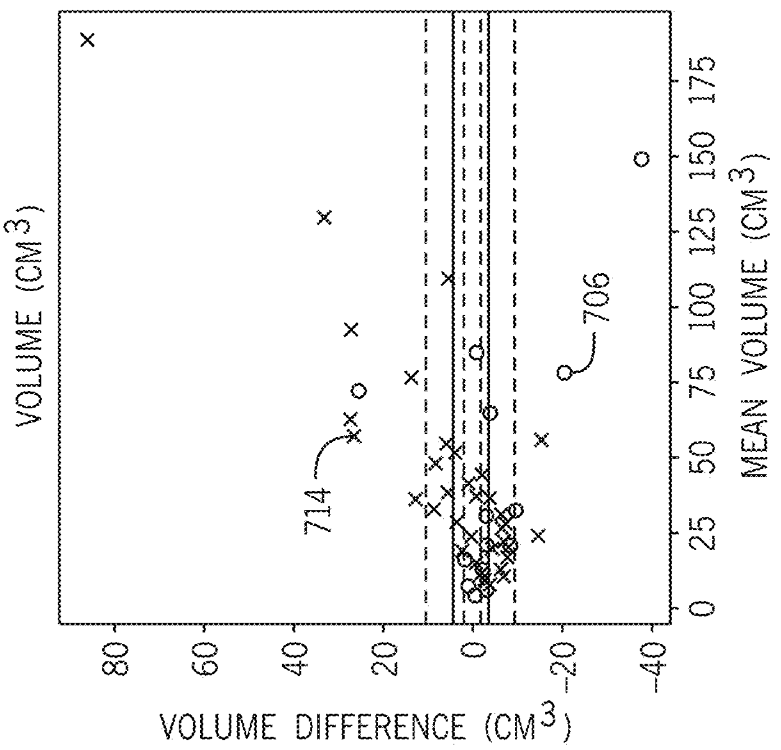
FIG. 7C illustrates volume difference for inter-reader and algorithm v. human performance for segmentation volume, for the system of FIG. 1.

FIG. 7A and FIG. 7C show examples of inter-reader agreement and Bland-Altman analysis for segmentation volumes. FIG. 7B and FIG. 7D show examples of inter-reader agreement and Bland-Altman analysis for length-normalized segmentation volume. FIG. 7A and FIG. 7B are examples of scatter plots with Intraclass Correlation Coefficients (ICC) shown. ICC is a descriptive statistic that describes the extent to which outcomes 1) within each cluster are likely to be similar or 2) between different clusters are likely to be different from each other, relative to outcomes from other clusters. Bland-Altman analysis is a method used to assess the agreement between two different quantitative measurements or techniques.

FIG. 7C and FIG. 7D show examples of Bland-Altman analyses. Lengths used for normalization were taken from the respective lumen indicators (e.g., 3D centerlines). Of the two summary statistics represented in FIG. 7A-FIG. 7D, total segmented volume shows higher inter-reader agreement, while length-normalized volume shows better human v. segmentation system 100 agreement. FIG. 7B shows an inter-reader length normalized volume measurement 704 compared to an algorithm v. human length normalized volume measurement 712. FIG. 7C shows an inter-reader mean difference of volume measurement 706 compared to an algorithm v. human mean difference of volume measurement 714.

Figure 8A:
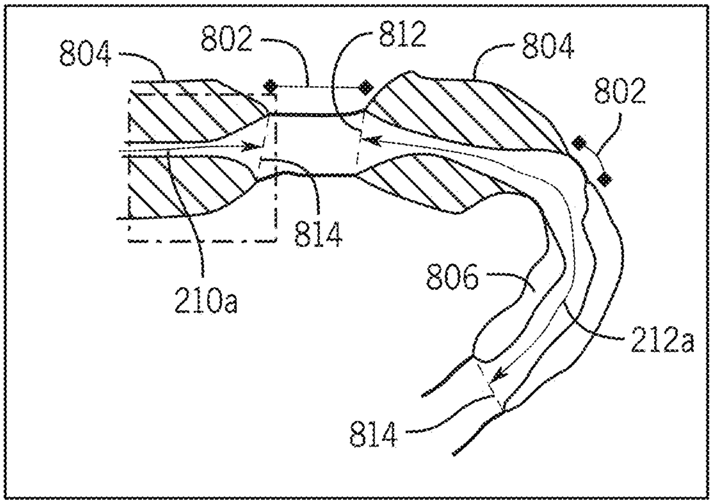
FIG. 8A-FIG. 8C illustrate examples of an annotation protocol for annotation with a lumen indicator identifying the length of abnormal bowel.
Figure 8B:
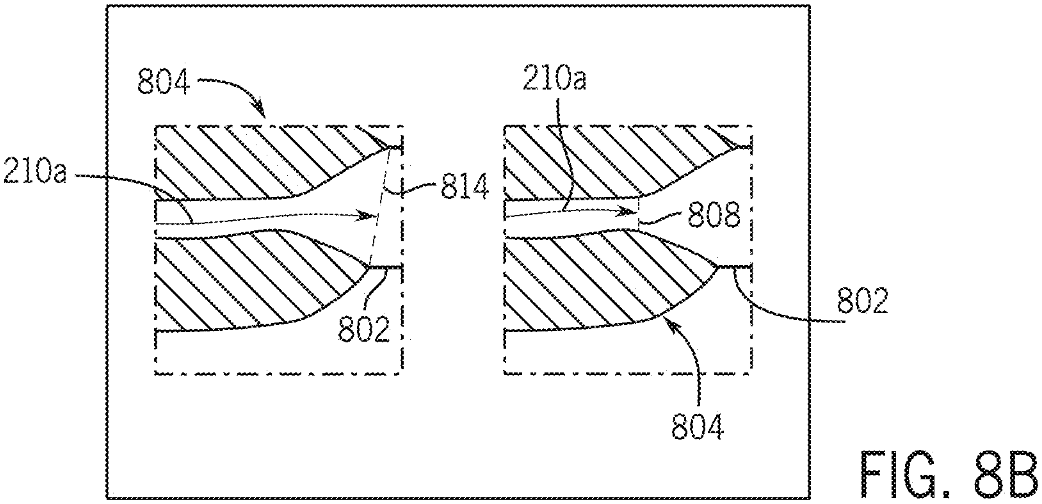
Figure 8C:
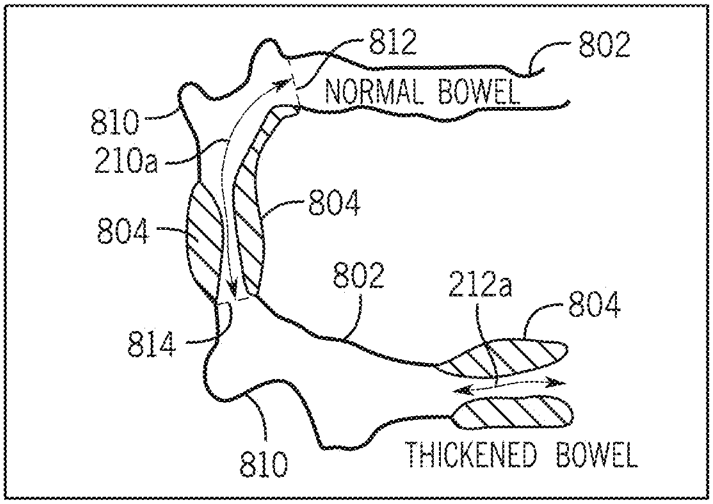

FIG. 8A-FIG. 8C show examples of an annotation protocol for use with lumen indicators (e.g., lumen indicator 210*a*/lumen indicator 212*a*) identifying the length of abnormal bowel. Each lumen indicator may begin or terminate at an extent. For example the lumen indicator 210*a*/212*a* may begin at a proximal extent 812 and end at a distal extent 814. In the example shown in FIG. 8A, a lumen indicator 210*a* and a lumen indicator 212*a*, as may be manually drawn by a medical provider 104, are shown. FIG. 8A shows a number of normal bowel segments (e.g., the normal bowel segment 802), abnormal bowel segment 804, and a thickened bowel segment 806. In some examples, a normal bowel segment 802 of a certain length (e.g., 3 cm) may be used to delineate between separate sections of abnormal bowel segments 804, and/or thickened bowel segments 806.

As shown for example in FIG. 8B, an extent typically should extend through an abnormal bowel segment 804 and across the lumen of the adjacent normal bowel segment 802. The left image in FIG. 8B shows a correctly drawn distal extent 814. The right image shows an incorrectly drawn premature extent 808 that ends within the lumen of the abnormal bowel segment 804.

As shown for example in FIG. 8C, where the abnormal bowel segment 804 is asymmetric, the lumen indicator 210*a* should start at a proximal part of the abnormal bowel segment 804 and end at the most distal part of the abnormal bowel segment 804. For example, the proximal extent 812 and/or distal extent 814 may be continued to a point where the wall of the bowel is normal around the lumen. See, e.g., the proximal extent 812 extending until normal bowel is present on both sides of the proximal extent 812. Also shown in FIG. 8C, pseudosacculation 810 may be ignored when placing points along the lumen indicator 210*a*/212*a* in an abnormal bowel segment 804 and can be considered normal otherwise.

Figure 9A:
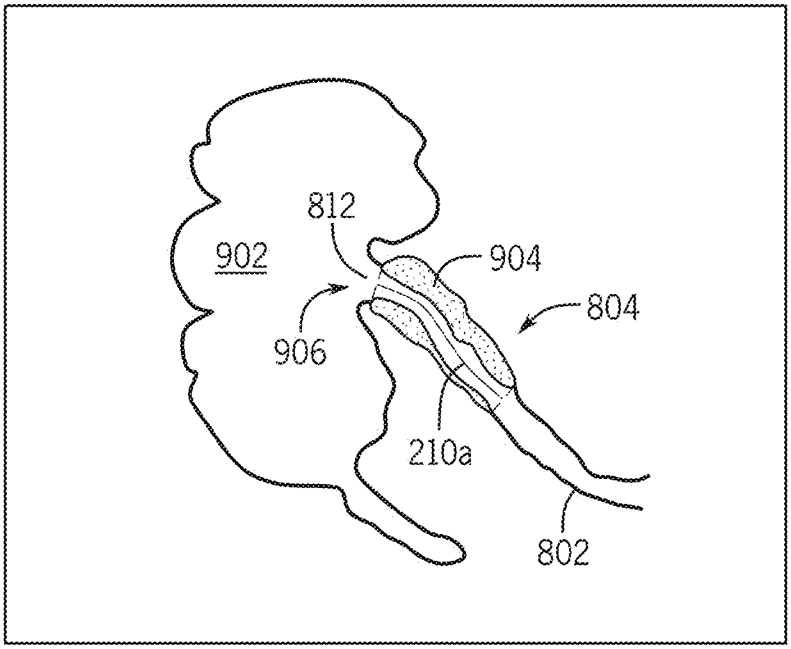
FIG. 9A-FIG. 9B illustrate examples of segmentation guidelines of the system of FIG. 1.
Figure 9B:
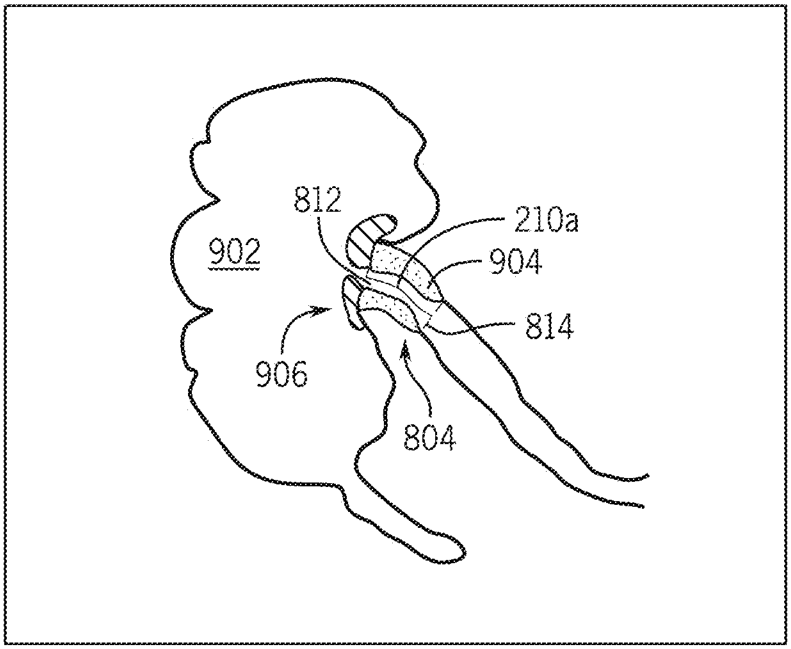

FIG. 9A and FIG. 9B examples of an annotation protocol for use with lumen indicators (e.g., lumen indicator 210*a*/lumen indicator 212*a*) near the ilcocaccal valve 906 of the stomach 902. As with other methods disclosed herein, a lumen indicator may be drawn over patient imaging 200, identifying the length of abnormal bowel. Where the disease includes the ilcocaccal valve, the distal extent of the abnormal terminal ileum 206 may end largely perpendicular to the ilcocaccal valve 906 in line with the colonic wall. The lumen indicator 210*a* may be drawn using techniques such as brush segmentation 904.

Figure 10:
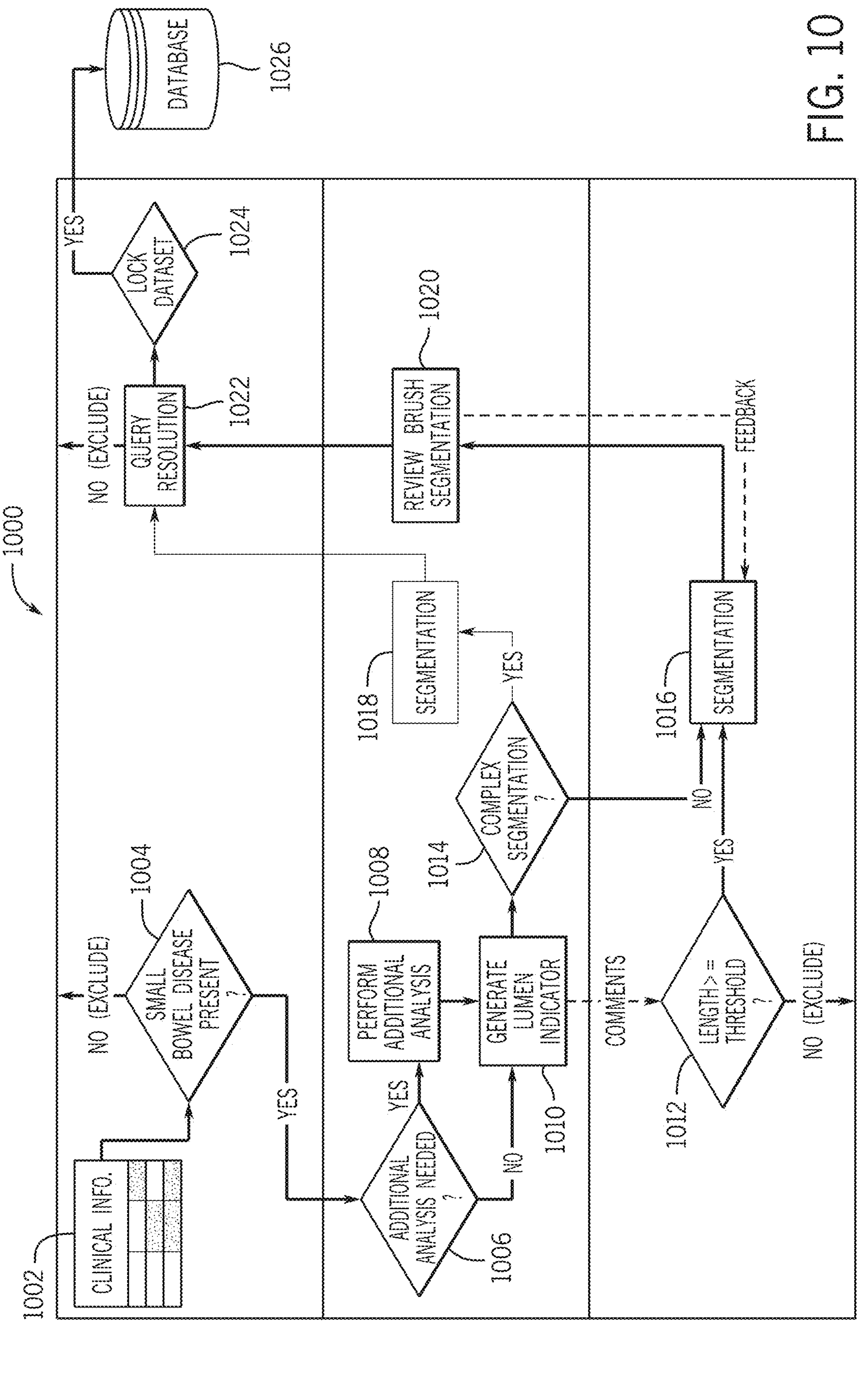
FIG. 10 illustrates an example method for training, validation, and testing the system of FIG. 1.

FIG. 10 illustrates an example method 1000 for segmenting portions of the bowel 204, including abnormal bowel segments 804, thickened bowel segments 806, and normal bowel segments 802. Although the example method 1000 depicts a particular sequence of operations, the sequence may be altered without departing from the scope of the present disclosure. For example, some of the operations depicted may be performed in parallel or in a different sequence that does not materially affect the function of the method 1000. In other examples, different components of an example device or system that implements the method 1000 may perform functions at substantially the same time or in a specific sequence.

In some examples, the method 1000 may be represented in computer code such as C, C++, Python, or other languages and may be compiled or passed to an interpreter for execution by one or more processors, such as a processing element 1302. In one example, the method 1000 may be written in Python and may undergo formal code review, e.g., compliant with ISO62304. To quantify algorithmic performance, standard segmentation metrics such as the Dice score (a metric for overlap of segmentations bounded between 0 and 1), the Symmetric Hausdorff Distance (SHD, the maximum distance between the outlines of two shapes) and the Mean Contour Distance (MCD, the average distance between the outlines of two shapes), may be calculated by the method 1000, as discussed herein.

The method 1000 may begin in operation 1004 and a patient 102 presents to a medical provider 104 with symptoms. The medical provider 104 may determine, or the patient 102 may provide, clinical information 1002, such as medical history, symptoms, demographic information (e.g., ethnicity, socioeconomic status, etc.) or biometric information (height, weight, blood pressure, etc.). The patient 102 may also include patient imaging 200, either determined by the imaging device 106 of the segmentation system 100 or by another system. If the symptoms are indicative of small bowel disease such as Crohn's disease, the method 1000 may proceed to operation 1006. If the symptoms are not associated with small bowel disease, the method 1000 may end.

In operation 1006, the patient imaging 200 may be captured by, or fed into, the segmentation system 100. For example, the imaging device 106 of the segmentation system 100 may be used to perform an MRE on the patient 102. The segmentation system 100 may determine if additional analysis is needed. For example, one form of additional analysis may include performing Magnetic Resonance Index of Activity (sMaRIA) analysis on the patient 102. If the segmentation system 100 determines that additional analysis is needed, the method 1000 may proceed to operation 1008.

In many embodiments, the operation 1008 may be optional. In operation 1008, additional analysis may be conducted. For example, a sMaRIA study may be completed. In other examples, additional imaging of the patient 102 may be completed with other imaging technologies, such as ultrasounds, CT scan, etc.

The method 1000 may proceed to operation 1010 from either operation 1006 or operation 1008. In the operation 1010, a user, such as a medical provider 104, may use the segmentation system 100 to generate one or more lumen indicators (e.g., the lumen indicator 210*a* or lumen indicator 212*a*). In many examples, the lumen indicator 210*a*, 212*a* may mark an interior portion of the lumen of the small intestine. Sec, e.g., the dashed lines in FIG. 2. In some examples, the lumen indicator 210*a*, 212*a* mark a line, line segment, curve, arc, spline, etc., and/or combinations or pluralities of these that extend along a portion of the lumen of the bowel. In some specific examples, the lumen indicator 210*a*, 212*a* are centerlines that extend along a portion of the small intestine. In some examples, the lumen indicator 210*a* and lumen indicator 212*a* are three-dimensional lines such as polylines, splines, or the like that indicate a centerline of the small intestine. In some examples, the lumen indicators are within the lumen, but not at the centerline. In some examples, one or more portions of the lumen indicator may intersect one or more portions of the bowel wall.

With reference to FIG. 2-FIG. 3B, the lumen indicator 210*a* optionally includes a marked portion 210*b* that indicates a possibly diseased portion of the bowel 204. Similarly, the lumen indicator 212*a* optionally includes a marked portion 212*b* that indicates a possibly diseased portion of the bowel 204. The marked portion 210*b*, marked portion 212*b* may be determined manually, such as by a medical provider 104 like a radiologist, gastroenterologist, technician, or the like.

For example, the medical provider 104 may interact with the user device 110 and mark sections of the bowel 204 that appear to be diseased. See, e.g., the nodes or dots on the solid lines covering the dashed lines. For example, the user device 110 may display successive slices of the ground truth data 202 and the medical provider 104 may mark (e.g., with a mouse, stylus, finger, or other input tool) a point in the slice that represents a one-dimensional lumen indicator. The segmentation system 100 may generate a polyline, spline, etc. through these successive point markers to generate a two dimensional or three dimensional lumen indicator 210*a*/212*a*. The medical provider 104 may mark the diseased portion either when marking each one-dimensional slice of the ground truth data 202, or may mark portions of the lumen indicator 210*a*/212*a* after the segmentation system 100 generates the same.

For example, a user such as a medical provider 104 may add a set of sequential points along the length of the lumen of an abnormal enteric segment. In some examples, the sequential points may be near a centerline of the lumen. In some embodiments, a cubic bezier curve may be generated between each adjacent pair of points (e.g., on different slices of the imaging study). The control points may be determined by enforcing C2 continuity (e.g., smoothness and differentiability of a curve, surface, or function) between adjacent curves, and solving for one or more curves simultaneously (e.g., by using the Thomas Algorithm AKA tridiagonal matrix algorithm). The resultant set of cubic Bezier curves is the lumen indicator 210*a*, lumen indicator 212*a* (see, e.g., FIG. 2 and FIG. 3A).

The method 1000 may proceed from operation 1010 to either operation 1014 or to operation 1012. The method 1000 may proceed to operation 1012, for example, if the segmentation system 100 determines that one or more lumen indicators could benefit from additional evaluation. In operation 1012, the segmentation system 100 compares the one or more lumen indicators generated in operation 1010 against a threshold. For example, the segmentation system 100 may compare the length of a lumen indicator against a length threshold. In one example, the segmentation system 100 compares the length of the lumen indicator against the threshold of 10 mm. In other examples, the segmentation system 100 may compare the length of the lumen indicator against thresholds such as 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18, mm, 19 mm, 20 mm, or longer. If the length of the lumen indicator is less than the threshold, that lumen indicator may be excluded from further analysis. If that is the only lumen indicator, the method 1000 may terminate. If there are additional lumen indicators, whose length is greater than or equal to the threshold, the method 1000 may continue to operation 1016 with respect to those lumen indicators.

The method 1000 may proceed from operation 1010 to operation 1014, for example, if the segmentation system 100 determines that one or more lumen indicators do not need additional evaluation, such as the length comparison performed in operation 1012. In operation 1014, the segmentation system 100 determines if the bowel 204 segmentation is complex. Examples of complex segmentation may include many segments, segments of diseased or abnormal bowel with segments of healthy bowel therebetween, asymmetric bowel disease, the presence of one or more pseudosacculations 810, etc. (e.g., as shown in FIG. 8C). If the segmentation system 100 determines in operation 1014 that that segmentation is not complex, the method 1000 may proceed to operation 1016. If the segmentation system 100 determines in operation 1014 that the segmentation is complex, the method 1000 may proceed to the operation 1018.

In operation 1016, the segmentation system 100 performs the automated segmentation described herein, e.g., as discussed with respect to FIG. 4A-FIG. 4D, and FIG. 11-FIG. 12, binarizing (thresholding) the voxels as discussed with respect to FIG. 5A-FIG. 5B, and the random forest regression. For example an AI/ML algorithm executed by a processing element 1302 of the segmentation system 100 analyzes the voxels of the patient imaging 200 surrounding each lumen indicator and determines whether the voxel should be included in the bowel segment model (e.g., the bowel segment model 302/bowel segment model 304) for the respective lumen indicator. The algorithm may rely on the previous training data set, ground truth data 202, the lumen indicators, and learning gained thereform.

Operation 1018 may be similar to operation 1016 in the use of an AI/ML model to analyze the voxels of the patient imaging 200 however, the algorithm may be specifically adapted to perform brush segmentation based on different training data (e.g., data for complex segmentations), or at higher resolution or a deeper neural net.

The method 1000 may proceed to operation 1020 and the segmentation system 100 optionally presents a system output 300, such as a bowel segment model for review to a medical provider 104. The medical provider 104 may decide to exclude or keep the particular system output 300. If the system output 300 is kept, the method 1000 may proceed to operation 1014 with respect to the system output 300. In some examples, in operation 1020, the segmentation system 100 may determine one or more quality metrics, such as an overlap or Dice score, the Symmetric Hausdorff Distance, the Mean Contour Distance, etc. may be calculated by the method 1000, as discussed herein.

The method 1000 may proceed from the operation 1018 or operation 1020 to operation 1022 and the segmentation system 100 examines the resolution of a system output 300 (e.g., a bowel segment model). If the resolution is below a threshold, the bowel segment model may be excluded. If the resolution is at or above a threshold, the method 1000 may proceed to operation 1024. For example, the segmentation system 100 may evaluate a number of voxels represented in a particular bowel segment model. If the number of voxels is below the threshold (e.g., below 100), the bowel segment model may be excluded.

The method 1000 may proceed to operation 1024 and the segmentation system 100 determines if the data set for a particular patient 102 should be locked. For example, if all of the lumen indicators generated in operation 1010 have either been analyzed and converted into bowel segment models or discarded, the data set may be locked. If the data set is incomplete or additional analysis is needed, the segmentation system 100 may continue to process the patient imaging 200, lumen indicators, and bowel segment models as discussed. If the data set is locked, the method 1000 may store the system output 300 and/or the patient imaging 200 in an database 114 for later analysis, retrieval, long term storage, and/or sharing with other medical providers 104.

Figure 11:
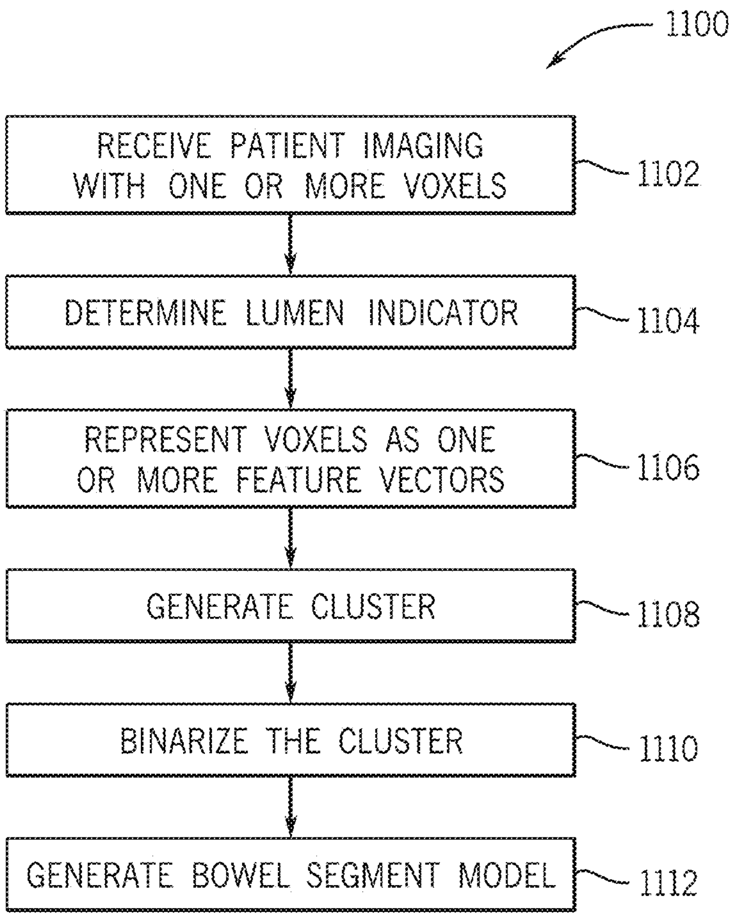
FIG. 11 illustrates a method for segmenting a bowel with the system of FIG. 1.

FIG. 11 is a flowchart illustrating a method 1100 for segmenting a bowel 204 with a segmentation system 100. Although the example method 1100 depicts a particular sequence of operations, the sequence may be altered without departing from the scope of the present disclosure. For example, some of the operations depicted may be performed in parallel or in a different sequence that does not materially affect the function of the method 1100. In other examples, different components of an example device or system that implements the method 1100 may perform functions at substantially the same time or in a specific sequence.

In operation 1102, the method 1100 receives patient imaging 200 including one or more voxels. In operation 1104, the segmentation system 100 determines a lumen indicator based on the patient imaging 200. In operation 1106, segmentation system 100 represents the one or more voxels within a threshold distance of the lumen indicator as one or more feature vectors. For example, the segmentation system 100 may include voxels within 0 mm (e.g., if a portion of the lumen indicator overlaps with a portion of the bowel 204 wall), 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18, mm, 19 mm, 20 mm, or longer (e.g., up to and including 50 mm) of a portion of the lumen indicator.

In operation 1108, the segmentation system 100 generates, based on the one or more feature vectors, a cluster including at least one of the one or move voxels. The clusters may be based on, or described by, one or more vectors or one or more of the following hyperparameters. Fifteen features originate from three sets of values based on the voxels in the cluster: raw voxel intensities; intensity after filtering with a Laplacian-of-Gaussian filter, kernel size (e.g., 2 mm); and 3D distance between each cluster 404,406 voxel and lumen indicator; and minimum, maximum, range, standard deviation, mean for each. Vectors may further include minimum 3D distance of the cluster 404, cluster 406 centroid from the respective lumen indicator 210*a*, lumen indicator 212*a*; difference between mean intensity of the cluster 404, 406 voxels, and the voxels surrounding the closest point where the respective lumen indicator intersects the current imaging plane; the minimum distance, in the direction orthogonal to the coronal plane, between the cluster 404, 406 and the lumen indicator 210*a*, lumen indicator 212*a*; the difference between mean of voxel intensities, and the mean of the voxel intensities within a threshold (e.g., three connected voxels (in-plane).

In operation 1110, segmentation system 100 binarizes the cluster into one or more groups based on a threshold value. In operation 1112, the segmentation system 100 generates a bowel segment model based at least on the cluster.

Figure 12:
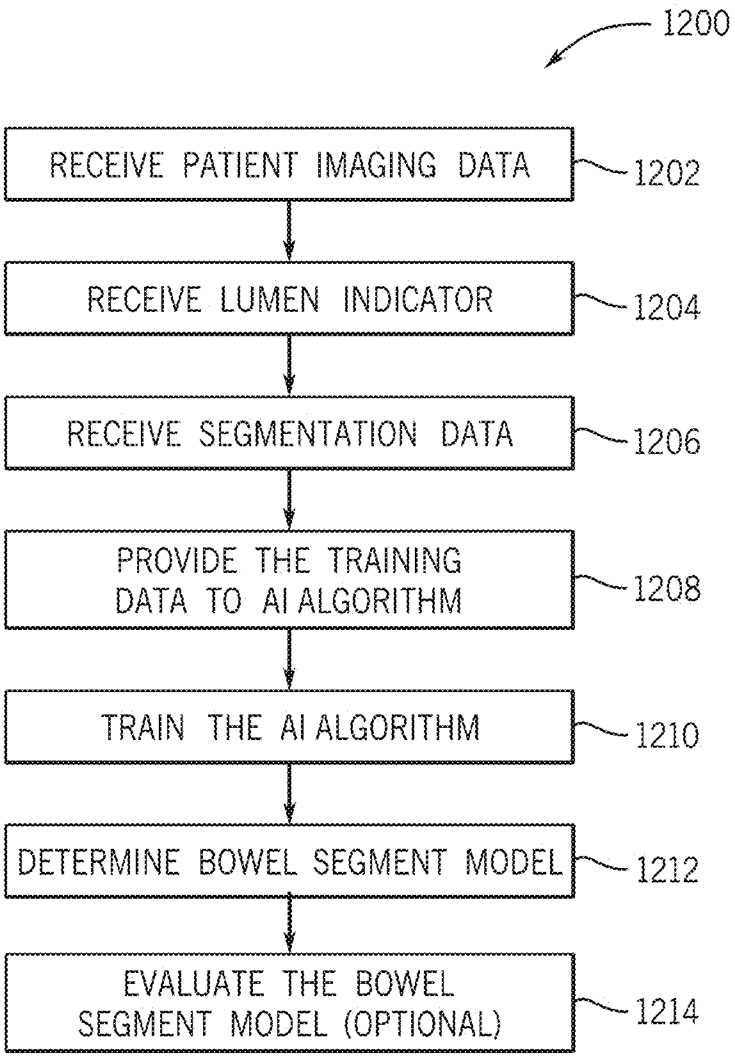
FIG. 12 illustrates a method for training an artificial intelligence model to segment portions of a bowel of a patient in accordance the system of FIG. 1.

FIG. 12 illustrates an example method 1200 for training an AI model of the segmentation system 100. Although the example method 1200 depicts a particular sequence of operations, the sequence may be altered without departing from the scope of the present disclosure. For example, some of the operations depicted may be performed in parallel or in a different sequence that does not materially affect the function of the method 1200. In other examples, different components of an example device or system that implements the method 1200 may perform functions at substantially the same time or in a specific sequence.

In operation 1202, a processing element of the segmentation system 100 receives, patient imaging 200 associated with a lumen. In operation 1204, the processing element receives a lumen indicator configured to mark a portion of the lumen. In operation 1206, the processing element receives segmentation data based on the lumen indicator. For example, the segmentation data may include one or more lumen indicators created as disclosed herein. Additionally, or alternately, the segmentation data may include manual segmentation data determined by the medical provider 104 using manual segmentation techniques. The patient imaging 200 data, the lumen indicator, and/or the segmentation data may be used as training data for the AI algorithm. In operation 1208, the processing element 1302 provides the training data to the AI algorithm.

In operation 1210, the processing element 1302 trains the AI algorithm using the training data to learn a correlation between the lumen indicator and the segmentation data associated with the lumen within the patient imaging 200. For example, the feature vectors for each cluster 404, cluster 406 are fed to a random forest regression model executed by a processing element of the segmentation system 100. The regressor may be trained as follows: training and validation sets may be used to generate clusters 404, 406 as described herein, and the degree of overlap with the ground truth data 202 quantified (e.g., the fraction of voxels within the cluster 404, 406 which were segmented in the ground truth data 202). A random forest regressor may be trained to predict this fraction based on the feature vector, for the training set. Modifications to the feature set, pipeline and hyperparameters may be based on results for the validation set.

In operation 1212, the processing element determines a bowel segment model based on the training data. In operation 1214, the processing element evaluates the bowel segment model based on validation data. For example, the processing element 1302 may compare the generated bowel segment model against the segmentation database such as by calculating one or more of a Dice score, a symmetric Hausdorff distance, a mean contour distance, a volume of the bowel segment model, or a length normalized volume of the bowel segment model.

Figure 13:
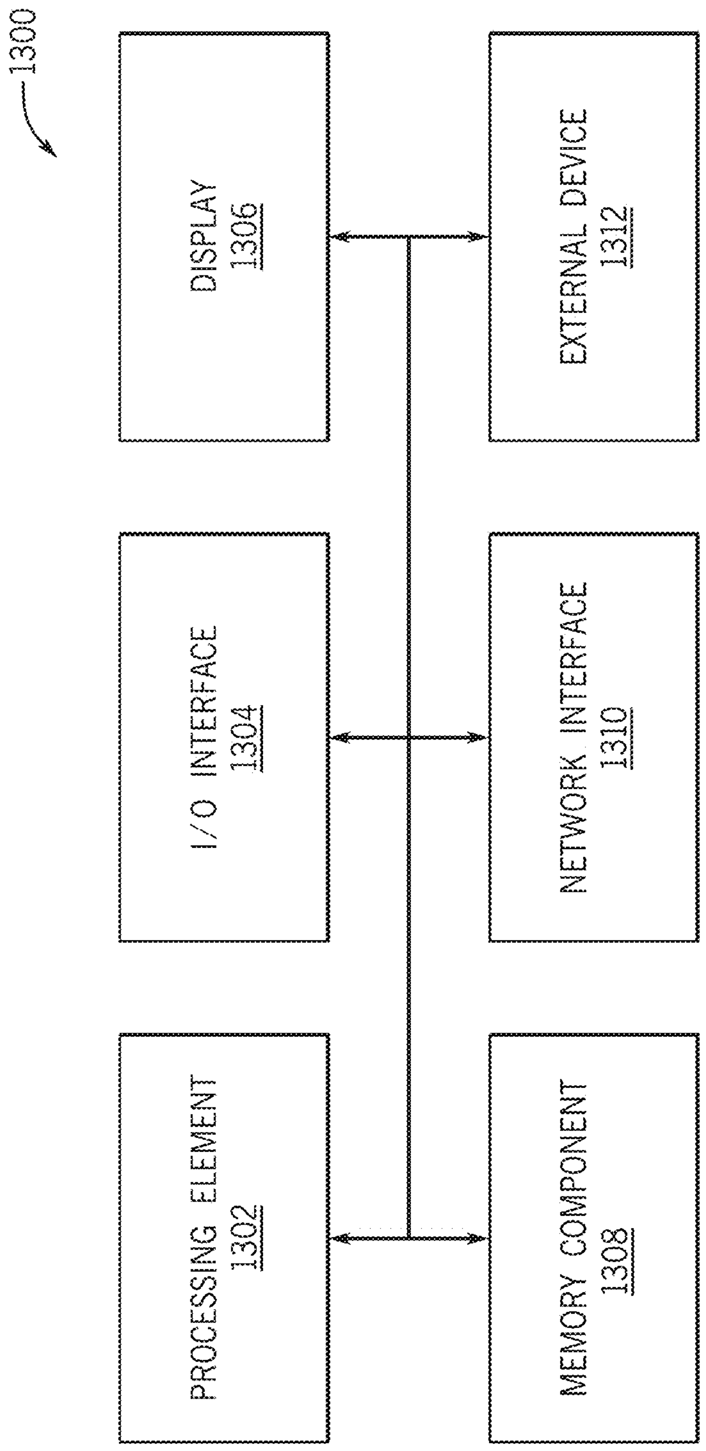
FIG. 13 is a simplified block diagram of components of the system of FIG. 1.

FIG. 13 is a simplified block diagram of components of a computing system 1300 of the segmentation system 100, such as the server 112, imaging device 106, user device 110, etc. The processing element 1302 and the memory component 1308 may be located at one or in several computing systems 1300. This disclosure contemplates any suitable number of such computing systems 1300. For example, the server 112 may be a desktop computing system, a mainframe, a blade, a mesh of computing systems 1300, a laptop or notebook computing system 1300, a tablet computing system 1300, an embedded computing system 1300, a system-on-chip, a single-board computing system 1300, or a combination of two or more of these. Where appropriate, a computing system 1300 may include one or more computing systems 1300; be unitary or distributed; span multiple locations; span multiple machines; span multiple data centers; or reside in a cloud, which may include one or more cloud components in one or more networks. A computing system 1300 may include one or more processing elements 1302, an input/output I/O interface 1304, one or more external devices 1312, one or more memory components 1308, and a network interface 1310. Each of the various components may be in communication with one another through one or more buses or communication networks, such as wired or wireless networks, e.g., the network 108. The components in FIG. 13 are exemplary only. In various examples, the computing system 1300 may include additional components and/or functionality not shown in FIG. 13.

The processing element 1302 may be any type of electronic device capable of processing, receiving, and/or transmitting instructions. For example, the processing element 1302 may be a central processing unit, microprocessor, processor, or microcontroller. Additionally, it should be noted that some components of the computing system 1300 may be controlled by a first processing element 1302 and other components may be controlled by a second processing element 1302, where the first and second processing elements may or may not be in communication with each other.

The I/O interface 1304 allows a user to enter data in to a computing system 1300, as well as provides an input/output for the computing system 1300 to communicate with other devices or services. The I/O interface 1304 can include one or more input buttons, touch pads, touch screens, and so on.

The external device 1312 are one or more devices that can be used to provide various inputs to the computing systems 1300, e.g., mouse, microphone, keyboard, trackpad, etc. The external devices 1312 may be local or remote and may vary as desired. In some examples, the external devices 1312 may also include one or more additional sensors.

The memory components 1308 are used by the computing system 1300 to store instructions for the processing element 1302 such as for executing the method 1000, an AI/ML algorithm, a user interface, as well as store data (e.g., patient imaging 200, ground truth data 202, system outputs 300, etc.). The memory components 1308 may be, for example, magneto-optical storage, read-only memory, random access memory, erasable programmable memory, flash memory, or a combination of one or more types of memory components.

The network interface 1310 provides communication to and from the computing system 1300 to other devices. The network interface 1310 includes one or more communication protocols, such as, but not limited to Wi-Fi, Ethernet, Bluetooth, etc. The network interface 1310 may also include one or more hardwired components, such as a Universal Serial Bus (USB) cable, or the like. The configuration of the network interface 1310 depends on the types of communication desired and may be modified to communicate via Wi-Fi, Bluetooth, etc.

The display 1306 provides a visual output for the computing system 1300 and may be varied as needed based on the device. The display 1306 may be configured to provide visual feedback to a user such as a patient 102 and/or a medical provider 104, and may include a liquid crystal display screen, light emitting diode screen, plasma screen, or the like. In some examples, the display 1306 may be configured to act as an input element for the user through touch feedback or the like.

Any description of a particular component being part of a particular embodiment, is meant as illustrative only and should not be interpreted as being required to be used with a particular embodiment or requiring other elements as shown in the depicted embodiment.

All relative and directional references (including top, bottom, side, front, rear, and so forth) are given by way of example to aid the reader's understanding of the examples described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

The present disclosure teaches by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

The technology described herein may be implemented as logical operations and/or modules in one or more systems. The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method comprising:

receiving patient imaging comprising one or more voxels;

determining a lumen indicator based on the patient imaging;

representing the one or more voxels within a distance of the lumen indicator as one or more feature vectors;

generating, based on the one or more feature vectors, a cluster comprising at least one of the one or move voxels;

binarizing the cluster into one or more groups based on a threshold overlap value; and generating a bowel segment model based at least on the binarized cluster.

2. The method of claim 1, wherein:

the one or more groups comprises at least a positive group and a negative group;

voxels in the positive group are included in the bowel segment model; and voxels in the negative group are excluded from the bowel segment model.

3. The method of claim 1, wherein the bowel segment model represents a segment of abnormal bowel.

4. The method of claim 1, wherein the patient imaging comprises at least one of a magnetic resonance image (MRI), an ultrasound, or a computer tomography (CT) image.

5. The method of claim 4, wherein the MRI comprises a noncontrast T2-weighted MRI image.

6. The method of claim 1, wherein the lumen indicator comprises a three-dimensional centerline of the lumen.

7. The method of claim 1, further comprising:

receiving segmentation data; and evaluating the bowel segment model based on the segmentation data.

8. The method of claim 7, wherein evaluating the bowel segment model comprises at least one of comparing the bowel segment model to the segmentation data.

9. The method of claim 8, wherein the comparison of the bowel segment model to the segmentation data comprises at least one of a Dice score, a symmetric Hausdorff distance, a mean contour distance, a volume, or a length normalized volume.

10. The patient of claim 9, wherein the length normalized volume is based at least in part on a length of the lumen indicator.

11. The method of claim 7, wherein the segmentation data comprises manual segmentation data determined by a medical provider.

12. A method for training an artificial intelligence (AI) model to segment portions of a bowel of a patient comprising:

receiving, by a processing element, patient imaging data associated with a lumen, wherein the patient imaging data comprises one or more voxels;

receiving, by the processing element, a lumen indicator configured to mark a portion of the lumen;

receiving, by the processing element, a segmentation data based on the lumen indicator, wherein the patient imaging data, the lumen indicator, and the segmentation data comprise training data;

providing the training data to an artificial intelligence algorithm executed by the processing element;

training, by the processing element, the artificial intelligence algorithm using the training data to learn a correlation between the lumen indicator and the segmentation data associated with the lumen within the patient imaging;

determining, by the processing element, a bowel segment model based on the training data, wherein determining the bowel segment model comprises:

representing the one or more voxels within a distance of the lumen indicator as one or more feature vectors;

generating, based on the one or more feature vectors, a cluster comprising at least one of the one or more voxels;

binarizing the cluster into one or more groups based on a threshold overlap value; and generating the bowel segment model based at least on the binarized cluster; and evaluating the bowel segment model based on a validation data.

13. The method of claim 12, wherein evaluating the bowel segment model comprises at least one of comparing the bowel segment model to the segmentation data.

14. The method of claim 13, wherein the segmentation data comprises manual segmentation data determined by a medical provider.

15. The method of claim 13, wherein the comparison of the bowel segment model to the segmentation data comprises at least one of a Dice score, a symmetric Hausdorff distance, a mean contour distance, a volume, or a length normalized volume.

16. A non-transitory computer-readable storage medium, the computer-readable storage medium including instructions that when executed by a processing element, cause the processing element to:

receive patient imaging comprising one or more voxels;

receive a lumen indicator based on the patient imaging;

represent the one or more voxels within a distance of the lumen indicator as one or more feature vectors;

generate, based on the one or more feature vectors, a cluster comprising at least one of the one or move voxels;

binarizing the cluster into one or more groups based on an overlap threshold value; and generate a bowel segment model based at least on the binarized cluster.

17. The non-transitory computer-readable storage medium of claim 16, wherein the bowel segment model represents a segment of abnormal bowel.

18. The non-transitory computer-readable storage medium of claim 16, wherein the patient imaging comprises at least one of a magnetic resonance image (MRI), an ultrasound, or a computer tomography (CT) image.

19. The non-transitory computer-readable storage medium of claim 16, wherein the lumen indicator comprises a three-dimensional centerline of the lumen.

* * * * *